United States Patent
Hendrix et al.

(10) Patent No.: US 7,202,243 B2
(45) Date of Patent: Apr. 10, 2007

(54) SUBSTITUTED IMIDAZOTRIAZINES

(75) Inventors: Martin Hendrix, Odenthal (DE); David Brückner, Essen (DE); Arno Friedl, Bergisch Gladbach (DE); Irene Gerlach, Weil am Rhein (DE); Volker Hinz, Köln (DE); Jörg Keldenich, Wuppertal (DE); Frank Mauler, Overath (DE); Ulrich Niewöhner, deceased, late of Wermelskirchen (DE); by Maria Niewöhner, legal representative, Wermelskirchen (DE); Dagmar Karthaus, Solingen (DE); Karl-Heinz Schlemmer, Wuppertal (DE); Adrian Tersteegen, Velbert (DE); Özkan Yalkinoglu, Wuppertal (DE)

(73) Assignee: Bayer HealthCare AG, Leverkusen (DE)

( * ) Notice: Subject to any disclaimer, the term of this patent is extended or adjusted under 35 U.S.C. 154(b) by 0 days.

(21) Appl. No.: 10/520,552

(22) PCT Filed: Jun. 25, 2003

(86) PCT No.: PCT/EP03/06661

§ 371 (c)(1),
(2), (4) Date: Oct. 19, 2005

(87) PCT Pub. No.: WO2004/005290

PCT Pub. Date: Jan. 15, 2004

(65) Prior Publication Data

US 2006/0166993 A1  Jul. 27, 2006

(30) Foreign Application Priority Data

Jul. 8, 2002  (DE) .......................... 102 30 605

(51) Int. Cl.
C07D 487/04  (2006.01)
A61K 31/53  (2006.01)
A61P 25/16  (2006.01)
A61P 25/18  (2006.01)

(52) U.S. Cl. ..................... 514/243; 544/184
(58) Field of Classification Search ............... 544/184; 514/243

See application file for complete search history.

(56) References Cited

U.S. PATENT DOCUMENTS 3,941,785 A   3/1976  Clarke et al.

FOREIGN PATENT DOCUMENTS

| EP | 1092719 | 4/2001 |
|----|---------|--------|
| WO | 9924433 | 5/1999 |
| WO | 03000269 | 3/2003 |
| WO | 03000693 | 3/2003 |

OTHER PUBLICATIONS

Siuciak et la., Neuropharmacology 1-11, 2006.*
Rodefer et al., Eur. J. Neurosci. 21(4): 1070-1076, 2005.*
Memory Pharmaceuticals Press Release Feb. 23, 2005, pp. 1-3.*
Cecil Textbook of Medicine, edited by Bennet, J.C., and Plum F., 20th edition, vol. 1, 1004-1010, 1996.*
West, Anthony R., Solid State Chemistry and its Applications, Wiley, New York, 1988, pp. 358 & 365.*
Vippagunta et al., Advanced Drug Delivery Reviews 48: 3-26, 2001.*
Molina, et al., "Fused Imidazoles: A Novel Synthesis of Imidazo[1,2-*b*][1,2,4]triazole and Imidazo[5,1-*f*]-[1,2,4]triazine Derivatives," *Synthesis, Georg Thieme Verlag, Stuggart*, 11, 843-847 (1989).

* cited by examiner

*Primary Examiner*—Venkataraman Balasubramanian

(57) ABSTRACT

The invention relates to new substituted imidazotriazines, processes for their preparation and their use for the production of medicaments for the treatment and/or prophylaxis of cancer and neurodegenerative disorders, in particular of Parkinson's disease and of schizophrenia.

8 Claims, No Drawings

SUBSTITUTED IMIDAZOTRIAZINES

This application is a 371 of PCT/EP2003/006661, filed Jun. 25, 2003.

The invention relates to new substituted imidazotriazines, processes for their preparation and their use for the production of medicaments for the treatment and/or prophylaxis of cancer and neurodegenerative disorders, in particular of Parkinson's disease and of schizophrenia.

The cyclic nucleotides cGMP and cAMP belong to the most important intracellular messenger substances. Phosphodiesterases (PDEs) play a significant role in the regulation of the concentrations of cGMP and cAMP. So far, 11 phosphodiesterase isoenzyme groups are known (PDE 1–7: Beavo et al. *Mol. Pharmacol.* 1994, 399–405; PDE 8–10: Soderling and Beavo *Curr. Opin. Cell Biol.* 2000, 12, 174–179; PDE 11: Fawcett et al. *Proc. Natl. Acad. Sci. U.S.A.* 2000, 97, 3702–3707).

PDE 10A hydrolyzes both cAMP and cGMP (Fujishige *J. Biol. Chem.* 1999, 274, 18438–18445). Transcribed PDE 10A was identified especially in the putamen and caudate nucleus regions of the brain, and in thyroid and testicular tissue. In comparison to normal tissue, the PDE 10A mRNA is moreover strongly expressed in certain tumor tissues, such as, for example, in tissues of breast, liver, colon and lung tumors.

Parkinson's disease is a chronically progressive, neurodegenerative disorder, which is characterized by the loss of dopaminergic neurones of the *substantia nigra*. The massive disorders of dopaminergic neurotransmission caused thereby lead to a serious malfunction of the movement-controlling extrapyramidal system. The main characteristics of early signs and symptoms of Parkinson's disease are resting tremor, slowing down of movements, muscle stiffness and unstable posture.

The present medications for Parkinson's disease are of purely symptomatic nature, substitution therapy with L-dopa being the most frequently used form of therapy.

Neither preventative nor restorative therapies are presently available (Mendis et al., *Can. J. Neurol. Sci.* 1999, 26, 89–103).

Idiopathic Parkinson's disease is a chronic, progressive neurological disorder, which belongs to a relatively wide classification of neurological diseases which are designated as parkinsonism. It is clinically defined by the occurrence of at least two of the four cardinal symptoms: bradykinesia, resting tremor, muscle stiffness and postural and movement disorders. Pathologically, the idiopathic form of Parkinson's disease is characterized by the loss of pigmented nerve cells, in particular in the area of the *substantia nigra* of the brain. Idiopathic Parkinson's disease makes up about 75% of all parkinsonism diseases. The other 25% of the cases are designated as atypical parkinsonism and include syndromes such as multiple system atrophy, striatonigral degeneration or vascular parkinsonism.

Schizophrenia is a chronic psychiatric disease which is characterized by psychoses, "negative symptoms" such as apathy and social seclusion, subtle cognitive deficits and lack of understanding of the illness. The etiology and the exact pathophysiology of schizophrenia and related schizoaffective disorders is still not known in detail even today (Kurachi, *Psychiatry Clin. Neurosci.* 2003, 57, 3–15; Lewis and Levitt, *Ann. Rev. Neurosci.* 2002, 25, 409–432). In postmortem investigations in the brain of schizophrenic individuals, abnormal cell distributions were found in various regions of the brain and altered brain activation patterns were seen in schizophrenia patients in neuroimaging studies (Goff et al., *Med. Clin. N. Am.* 2001, 85, 663–689). There are indications that cGMP could be involved in the pathogenesis of psychoses. Thus, Gattaz and coworkers (Gattaz et al., *Br. J. Psychiatry* 1983, 142, 288–291) reported that the levels of cGMP in the cerebrospinal fluid of schizophrenic patients are altered. Moreover, it was shown that the administration of the classic antipsychotic haloperidol increases the cGMP content of the cerebrospinal fluid (Gattaz et al., *Biol. Psychiatry* 1984, 19, 1229–35).

Although the details of the neuroanatomic basis of schizophrenic disorders are still the subject of medical research, it was possible to show that, inter alia, the basal ganglia play an important role in these diseases (e.g. Shenton et al., *Schizophr. Res.* 2001, 49, 1–52).

The synthesis of 4-amino-2,5-diphenyl-7-methylthioimidazo[5,1-f][1,2,4]triazines is known from *Synthesis* 1989, 843–847.

In U.S. Pat. No. 3,941,785, 2-aminoimidazo[5,1-f][1,2,4]triazines are described as PDE inhibitors having spasmolytic action for the treatment of asthma, bronchitis, chronic heart failure and skin diseases.

EP-A 1 250 923 describes the use of selective PDE10 inhibitors, such as, for example, papaverine, for the treatment of diseases of the central nervous system, such as, for example, Parkinson's disease.

The present invention relates to compounds of the formula (I),

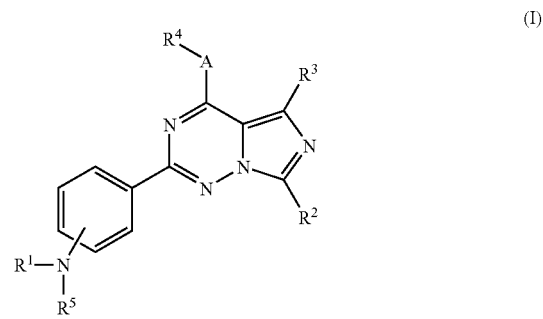

in which $R^1$ denotes hydrogen or $C_1$–$C_6$-alkyl, $R^5$ denotes hydrogen, formyl, $C_1$–$C_6$-alkyl, ($C_1$–$C_6$-alkyl)carbonyl, $C_1$–$C_6$-alkyl-sulfonyl, $C_3$–$C_8$-cycloalkylcarbonyl or (3- to 8-membered heterocyclyl)-carbonyl, where alkylcarbonyl can be substituted by up to 3 substituents—independently of one another selected from the group consisting of halogen, hydroxyl, amino, carboxyl, $C_1$–$C_6$-alkoxy, $C_6$–$C_{10}$-aryl, $C_1$–$C_6$-alkylamino and a 3- to 8-membered heterocyclyl substituted by up to 3 $C_1$–$C_3$-alkyl-substituents—, or $R^1$ and $R^5$, together with the nitrogen atom to which they are bonded, denote a 5- to 8-membered heterocycle, which can be substituted by up to 3 substituents—independently of one another selected from the group consisting of halogen, hydroxyl, $C_1$–$C_6$-alkyl, $C_1$–$C_6$-alkoxy, $C_6$–$C_{10}$-aryl, amino and $C_1$–$C_6$-alkylamino—, $R^2$ denotes $C_1$–$C_6$-alkyl or $C_3$–$C_4$-cycloalkyl, $R^3$ denotes methyl, A denotes an oxygen atom or NH, and R⁴ denotes $C_6$–$C_{10}$-aryl, which can be substituted by up to 3 substituents—independently of one another selected from the group consisting of halogen, formyl, carboxyl, carbamoyl, cyano, hydroxyl, trifluoromethyl, trifluoromethoxy, nitro, $C_1$–$C_6$-alkyl, $C_1$–$C_6$-alkoxy, 1,3-dioxapropane-1,3-diyl, $C_1$–$C_6$-alkylthio and —NR⁶R⁷—, in which R⁶ and R⁷ independently of one another represent hydrogen, $C_1$–$C_6$-alkyl or ($C_1$–$C_6$-alkyl)carbonyl, and their salts, solvates or solvates of the salts.

Depending on their structure, the compounds according to the invention can exist in stereoisomeric forms (enantiomers, diastereomers). The invention therefore relates to the enantiomers or diastereomers and their respective mixtures. The stereoisomerically uniform constituents can be isolated in a known manner from such mixtures of enantiomers and/or diastereomers.

Salts which are preferred in the context of the invention are physiologically acceptable salts of the compounds (I).

Physiologically acceptable salts of the compounds (I) include acid addition salts of mineral acids, carboxylic acids and sulfonic acids, e.g. the salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, propionic acid, lactic acid, tartaric acid, malic acid, citric acid, fumaric acid, maleic acid and benzoic acid.

Physiologically acceptable salts of the compounds (I) also include salts of customary bases, such as, by way of example and preferably, alkali metal salts (e.g. sodium and potassium salts), alkaline earth metal salts (e.g. calcium and magnesium salts) and ammonium salts, derived from ammonia or organic amines having 1 to 16 C atoms, such as, by way of example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dehydroabietylamine, arginine, lysine, ethylenediamine and methylpiperidine.

Solvates in the context of the invention are designated as those forms of the compounds which in the solid or liquid state form a complex by coordination with solvent molecules. Hydrates are a special form of the solvates, in which the coordination takes place with water.

In the context of the present invention the substituents, if not stated otherwise, have the following meaning:

$C_1$–$C_6$-Alkoxy represents a straight-chain or branched alkoxy radical having 1 to 6, preferably 1 to 4, particularly preferably having 1 to 3 carbon atoms. Nonlimiting examples include methoxy, ethoxy, n-propoxy, isopropoxy, tert-butoxy, n-pentoxy and n-hexoxy.

$C_1$–$C_6$-Alkylamino represents a straight-chain or branched alkylamino radical having 1 to 6, preferably 1 to 4, particularly preferably having 1 to 3 carbon atoms. Nonlimiting examples include methylamino, ethylamino, n-propylamino, isopropylamino, tert-butylamino, n-pentylamino and n-hexylamino, dimethylamino, diethylamino, di-n-propylamino, diisopropylamino, di-t-butylamino, di-n-pentylamino, di-n-hexylamino, ethylmethylamino, isopropylmethylamino, n-butylethylamino, n-hexyl-i-pentylamino.

$C_1$–$C_6$-Alkyl represents a straight-chain or branched alkyl radical having 1 to 6, preferably 1 to 4, particularly preferably 1 to 3 carbon atoms. Nonlimiting examples include methyl, ethyl, n-propyl, isopropyl, tert-butyl, n-pentyl and n-hexyl.

($C_1$–$C_6$-Alkyl)carbonyl represents a straight-chain or branched alkylcarbonyl radical having 1 to 6, preferably 1 to 4, particularly preferably 1 to 3 carbon atoms. Nonlimiting examples include acetyl, ethylcarbonyl, propylcarbonyl, isopropylcarbonyl, butylcarbonyl, isobutylcarbonyl, pentylcarbonyl and hexylcarbonyl.

(3- to 8-membered cycloalkyl)carbonyl represents a monocyclic cycloalkyl bonded via a carbonyl group. Nonlimiting examples include cyclopropylcarbonyl, cyclobutylcarbonyl, cyclopentylcarbonyl, cyclohexylcarbonyl and cycloheptyl-carbonyl.

(3- to 8-membered heterocyclyl)carbonyl represents a heterocyclyl bonded via a carbonyl group. Nonlimiting examples include tetrahydrofuran-2-ylcarbonyl, pyrrolidin-2-ylcarbonyl, pyrrolidin-3-ylcarbonyl, pyrrolinylcarbonyl, piperidinyl-carbonyl, morpholinylcarbonyl and perhydroazepinylcarbonyl.

$C_1$–$C_6$-Alkylsulfonyl represents a straight-chain or branched alkylsulfonyl radical having 1 to 6, preferably 1 to 4, particularly preferably 1 to 3 carbon atoms. Nonlimiting examples include methylsulfonyl, ethylsulfonyl, n-propylsulfonyl, isopropylsulfonyl, tert-butylsulfonyl, n-pentylsulfonyl and n-hexylsulfonyl.

$C_1$–$C_6$-Alkylthio represents a straight-chain or branched alkylthio radical having 1 to 6, preferably 1 to 4, particularly preferably 1 to 3 carbon atoms. Nonlimiting examples include methylthio, ethylthio, n-propylthio, isopropylthio, tert-butylthio, n-pentylthio and n-hexylthio.

$C_6$–$C_{10}$-Aryl represents an aromatic radical having 6 to 10 carbon atoms. Nonlimiting examples include phenyl and naphthyl.

Halogen represents fluorine, chlorine, bromine and iodine. Fluorine, chlorine and bromine are preferred, particularly preferably fluorine and chlorine.

3- to 8-membered heterocyclyl represents a mono- or polycyclic, preferably mono- or bicyclic, nonaromatic radical as a rule having 4 to 8, preferably 5 to 8, ring atoms and up to 3, preferably up to 2 hetero atoms or hetero groups from the group consisting of N, O, S, SO, $SO_2$. The heterocyclyl radicals can be saturated or partially unsaturated. Nonlimiting examples include 5- to 8-membered, monocyclic saturated heterocyclyl radicals having up to two hetero ring atoms from the group consisting of O, N and S such as tetrahydrofuran-2-yl, pyrrolidin-2-yl, pyrrolidin-3-yl, pyrrolinyl, piperidinyl, morpholinyl, perhydroazepinyl.

5- to 8-membered heterocycle represents a mono- or polycyclic, heterocyclic radical having 5 to 8 ring atoms and up to 3, preferably 2, hetero atoms or hetero groups from the group consisting of N, O, S, SO, $SO_2$, where at least one of the hetero atoms or hetero groups is a nitrogen atom. 5- to 7-membered heterocyclyl is preferred. Mono- or bicyclic heterocyclyl is preferred. Monocyclic heterocyclyl is particularly preferred. As hetero atoms, O, N and S are preferred. The heterocyclyl radicals can be saturated or partially unsaturated. Saturated heterocyclyl radicals are preferred. 5- to 7-membered, monocyclic saturated heterocyclyl having up to two hetero atoms from the group consisting of O, N and S is particularly preferred. Nonlimiting examples include pyrrolinyl, piperidinyl, morpholinyl, perhydroazepinyl.

$C_3$–$C_4$-Cycloalkyl represents monocyclic cycloalkyl, such as, for example, cyclo-propyl and cyclobutyl.

If radicals in the compounds according to the invention are optionally substituted, if not specified otherwise a substitution by up to three identical or different substituents is preferred.

The compounds according to the invention can also be present as tautomers, as is shown by way of example below for A=NH:

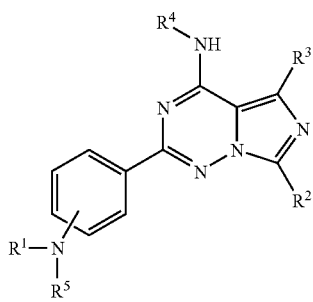

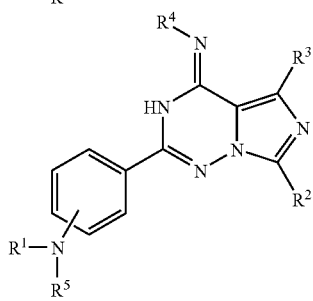

A further embodiment of the invention relates to compounds of the formula (I), in which $R^1$ denotes hydrogen, $R^5$ denotes hydrogen, $(C_3-C_6$-cycloalkyl)carbonyl, (4- to 6-membered heterocyclyl)carbonyl or $(C_1-C_3$-alkyl)carbonyl, where alkylcarbonyl can be monosubstituted by hydroxyl or amino, $R^2$ denotes $C_1-C_6$-alkyl, $R^3$ denotes methyl, A denotes an oxygen atom or NH, and $R^4$ denotes phenyl, which can be substituted by up to 3 substituents, independently of one another selected from the group consisting of halogen, $C_1-C_6$-alkyl and $C_1-C_6$-alkoxy, and their salts, solvates or solvates of the salts.

A further embodiment of the invention relates to compounds of the formula (I), in which $R^5$ denotes hydrogen, $(C_3-C_6$-cycloalkyl)carbonyl, (4- to 6-membered heterocyclyl)carbonyl or $(C_1-C_3$-alkyl)carbonyl, where alkylcarbonyl can be monosubstituted by hydroxyl or amino, and $R^1$, $R^2$, $R^3$, $R^4$ and A have the abovementioned meanings and their salts, solvates or solvates of the salts.

A further embodiment of the invention relates to compounds of the formula (I), in which $R^2$ denotes $C_1-C_6$-alkyl, and $R^1$, $R^5$, $R^3$, $R^4$ and A have the abovementioned meanings and their salts, solvates or solvates of the salts.

A further embodiment of the invention relates to compounds of the formula (I), in which $R^4$ denotes phenyl, which can be substituted by 1 to 3 $(C_1-C_6)$-alkoxy radicals, and $R^1$, $R^5$, $R^2$, $R^3$ and A have the abovementioned meanings and their salts, solvates or solvates of the salts.

A further embodiment of the invention relates to compounds of the formula (I), in which $R^4$ denotes 3,4,5-trimethoxyphenyl, and $R^1$, $R^5$, $R^2$, $R^3$ and A have the abovementioned meanings.

The invention furthermore relates to processes for the preparation of the compounds according to the invention by reaction of

[A] compounds of the formula (II),

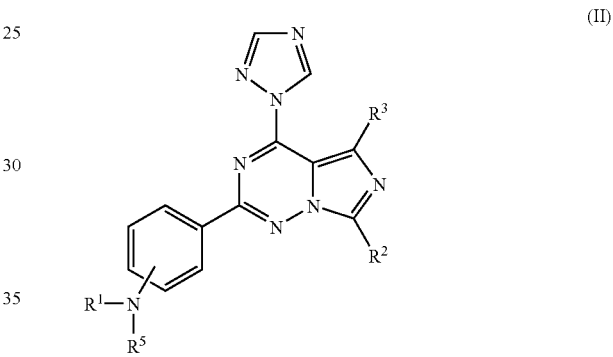

in which $R^1$, $R^5$, $R^2$ and $R^3$ have the meaning indicated above, with compounds of the formula (III),

in which $R^4$ and A have the meaning indicated above, or

[B] compounds of the formula (Ia),

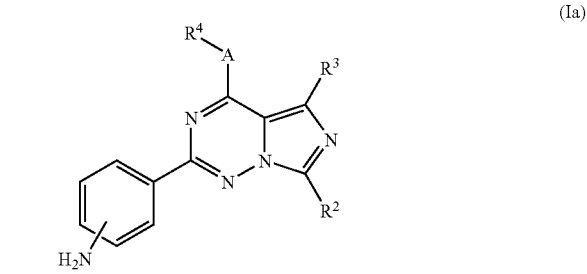

in which
R², R³, R⁴ and A have the meaning indicated above,
with compounds of the formula (IV),

(IV)

in which
R⁵ has the meaning indicated above and
X¹ represents halogen, preferably bromine or chlorine, or hydroxyl,
to give compounds of the formula (Ib),

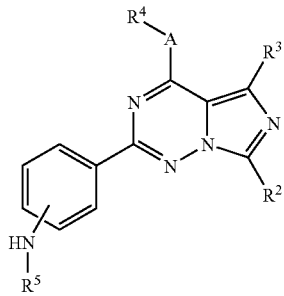
(Ib)

in which
R⁵, R², R³, R⁴ and A have the meanings indicated above,
or
[C] compounds of the formula

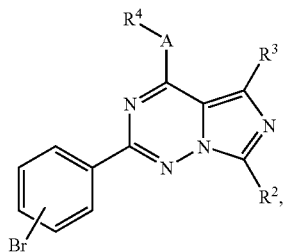
(V)

in which
R², R³, R⁴ and A have the meanings indicated above,
with compounds of the formula (VI),

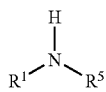
(VI)

in which
R¹ and R⁵ have the meaning indicated above
and a further reaction of the resulting compounds (I) optionally with the appropriate (i) solvents and/or (ii) bases or acids to give their solvates, salts or solvates of the salts.

The reaction according to process [A] can in general be carried out in inert solvents, if appropriate in the presence of base and auxiliary reagents, preferably in a temperature range from 20 to 120° C. at normal pressure or without solvent in the melt.

Auxiliary reagents are, for example, potassium fluoride or dimethylaminopyridine, or/and crown ethers, preferably 15-crown-5, 18-crown-8 or 12-crown-4.

The reaction according to process [B] can, if X¹ represents halogen, in general be carried out at normal pressure in inert solvents, if appropriate in the presence of a base, preferably in a temperature range from 0° C. to 50° C.

If X¹ represents hydroxyl, the reaction can in general be carried out at normal pressure in inert solvents, if appropriate in the presence of a base, in the presence of customary condensing agents, preferably in a temperature range from 20° C. to 50° C.

Condensing agents are, for example, carbodiimides such as, for example, N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexyl-carbodiimide-N'-propyloxymethylpolystyrene (PS carbodiimide) or carbonyl compounds such as carbonyldiimidazole, or 1,2-oxazolium compounds such as 2-ethyl-5-phenyl-1,2-oxazolium 3-sulfate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxytri(dimethylamino)phosphonium hexafluorophosphate, or O-(benzotriazol-1-yl)-N,N,N',N'-tetra-methyluronium hexafluorophosphate (HBTU), 2-(2-oxo-1-(2H)pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or mixtures of these compounds.

The combination of N-(3-dimethylaminoisopropyl)-N'-ethylcarbodiimide hydrochloride (EDC) and 1-hydroxybenzotriazole (HOBt), and the combination of benzotriazol-1-yloxytris(dimethylamino)phosphonium hexafluorophosphate (BOP) and triethylamine is particularly preferred.

Inert solvents for processes [A] and [B] are, for example, halogenohydrocarbons such as methylene chloride, trichloromethane, tetrachloromethane, trichloroethane, tetrachloroethane, 1,2-dichloroethane or trichloroethylene, ethers such as diethyl ether, methyl tert-butyl ether, dioxane, tetrahydrofuran, 1,2-dimethoxyethane, or diethylene glycol dimethyl ether, hydrocarbons such as benzene, xylene, toluene, hexane, cyclohexane or petroleum fractions, or nitroalkanes such as nitromethane, or carboxylic acid esters such as ethyl acetate, n-alkylated carboxamides such as dimethylformamide, dimethylacetamide, or ketones such as acetone, 2-butanone, or alkyl sulfoxides such as dimethyl sulfoxide, or alkylnitriles such as acetonitrile or heteroaromatics such as pyridine. For process [A], pyridine, glycol dimethyl ether, tetrahydrofuran, dioxane or dimethyl sulfoxide are preferred and for process [B], if X¹ represents halogen, tetrahydrofuran or methylene chloride and, if X¹ represents hydroxyl, tetrahydrofuran, dimethylformamide or methylene chloride are preferred.

Bases for processes [A] and [B] are, for example, alkali metal hydroxides such as sodium hydroxide or potassium hydroxide, alkali metal carbonates such as cesium carbonate, sodium carbonate or potassium carbonate, alkali metal alkoxides such as sodium methoxide or potassium methoxide, sodium ethoxide or potassium ethoxide or potassium tert-butoxide, amides such as sodium amide, lithium bis-(trimethylsilyl)amide, lithium diisopropylamide, organometallic compounds such as butyllithium or phenyllithium, alkali metal hydrides such as sodium hydride, alkylamines such as triethylamine or diisopropylethylamine, N-methylmorpholine, N-methylpiperidine, 4-dimethylaminopyridine, or DBU. For process [A], sodium hydride, triethylamine, potassium tert-butoxide or DBU are preferred, and for process [B], if $X^1$ represents halogen, triethylamine is preferred.

The reaction according to process [C] is in general carried out in inert solvents, if appropriate in the presence of a base, in the presence of catalysts, preferably in a temperature range from 50 to 150° C. to the at normal pressure.

Inert solvents are, for example, hydrocarbons such as benzene, xylene, toluene; toluene is preferred.

Bases are, for example, alkali metal alkoxides such as potassium tert-butoxide or alkali metal carbonates such as cesium carbonate, sodium carbonate or potassium carbonate.

Catalysts are palladium complexes which can be employed preformed or generated in situ from a suitable palladium source, such as, for example, bis(dibenzylideneacetone)palladium(0) or tetrakis-triphenylphosphinepalladium(0) and a suitable phosphine ligand. The use of 2,2'-bis(diphenylphosphino)-1,1'-binaphthalene (BINAP) as a phosphine ligand is particularly preferred.

The compounds (III), (IV) and (VI) are known or can be synthesized from the corresponding starting materials analogously to known processes.

The compounds (V) can be prepared analogously to process [A] using the corresponding starting materials.

For the preparation of the compounds (Ia), compounds of the formula (VII),

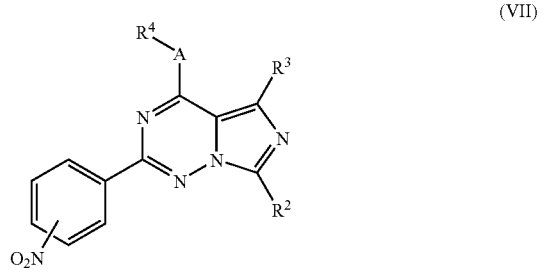

(VII)

in which $R^2$, $R^3$, $R^4$ and A have the meanings indicated above, can be reacted with reductants and, if appropriate, in the presence of catalysts, such as palladium on active carbon.

The reaction is in general carried out in inert solvents, preferably in a temperature range from 20 to 150° C. at normal pressure to 3 bar.

Reductants are, for example, hydrogen, tin dichloride or titanium trichloride; hydrogen or tin dichloride is preferred.

Inert solvents are, for example, ethers such as diethyl ether, methyl tert-butyl ether, 1,2-dimethoxyethane, dioxane, tetrahydrofuran or diethylene glycol dimethyl ether, alcohols such as methanol, ethanol, n-propanol, isopropanol, n-butanol or tert-butanol, hydrocarbons such as benzene, xylene, toluene, hexane, cyclohexane or petroleum fractions, amides such as dimethylformamide, dimethylacetamide, alkylnitriles such as acetonitrile, heteroaromatics such as pyridine; methanol, ethanol, isopropanol or (when using tin dichloride) dimethylformamide are preferred.

Compounds (VII) can be prepared analogously to process [A] using the corresponding starting materials.

For the preparation of the compounds (II), compounds of the formula (VIII),

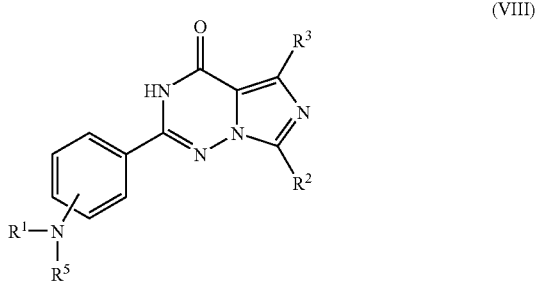

(VIII)

in which $R^1$, $R^5$, $R^2$ and $R^3$ have the meanings indicated above, can be reacted with 1,2,4-triazole in the presence of a chlorinating agent, preferably phosphorus oxychloride, phosphorus pentachloride, sulfuryl chloride and/or thionyl chloride.

The reaction is in general carried out in inert solvents, if appropriate in the presence of a base, preferably in a temperature range from −20° C. to 20° C. at normal pressure (cf, for example, Knutsen et al., *J. Chem. Soc., Perkin Trans* 1, 1985, 621–630; A. Kraszewski, J. Stawinski, *Tetrahedron Lett.* 1980, 21, 2935).

For the reaction, the inert solvents of the type mentioned for processes [A] and [B] can be used; pyridine, trichloromethane, diethylphenylamine, dioxane or acetonitrile are preferred.

As bases, those recommended for processes [A] and [B] can be used; triethylamine, pyridine or diethylphenylamine are preferred.

For the preparation of the compounds (VIII), compounds of the formula (IX),

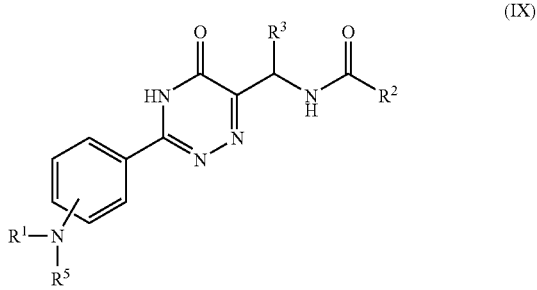

(IX)

in which $R^1$, $R^5$, $R^2$ and $R^3$ have the meanings indicated above, can be reacted with suitable dehydrating reagents (e.g. Lewis acids), preferably phosphorus oxychloride, phosphorus pentoxide, phosphoric acid or methylsulfonyl chloride.

The reaction is in general carried out in inert solvents, preferably in a temperature range from 40 to 80° C. at normal pressure (cf., for example, Charles et al. *J. Chem. Soc., Perkin Trans* 1, 1980, 1139).

Suitable inert solvents are those mentioned for processes [A] and [B]; 1,2-dichloroethane is preferred.

For the preparation of the compounds (IX), compounds of the formula (X),

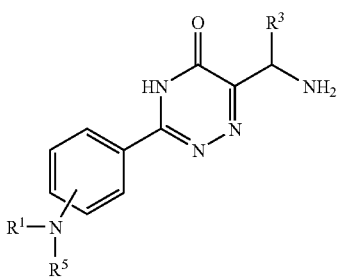

(X)

or their salts, e.g. hydrochloride salts, in which

R$^1$, R$^5$ and R$^3$ have the meanings indicated above, can be reacted with compounds of the formula (XI),

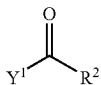

(XI)

in which

R$^2$ has the meaning indicated above and

Y$^1$ represents halogen, preferably bromine or chlorine, or hydroxyl.

If Y$^1$ represents halogen, the reaction can in general be carried out in inert solvents, if appropriate in the presence of a base, preferably in a temperature range from 0° C. to 50° C. at normal pressure.

Suitable inert solvents are those mentioned for processes [A] and [B]; tetrahydrofuran or methylene chloride is preferred.

Suitable bases are those recommended for processes [A] and [B]; preferably triethylamine.

If Y$^1$ represents hydroxyl, the reaction can in general be carried out in inert solvents, if appropriate in the presence of a base, in the presence of customary condensing agents, preferably in a temperature range from 20° C. to 50° C. at normal pressure.

Suitable inert solvents are those mentioned for processes [A] and [B]; tetrahydrofuran, dimethylformamide or methylene chloride is preferred.

Suitable condensing agents are those recommended for process [B] or mixtures of these.

Suitable bases are those mentioned for processes [A] and [B].

The combination of N-(3-dimethylaminoisopropyl)-N'-ethylcarbodiimide hydrochloride (EDC) and 1-hydroxybenzotriazole (HOBt), and the combination of benzotriazol-1-yloxytris(dimethylamino)phosphonium hexafluorophosphate (BOP) and triethylamine is particularly preferred.

The compounds (XI) are known or can be synthesized from the corresponding starting materials according to known processes.

For the preparation of the compounds (X), compounds of the formula (IXa),

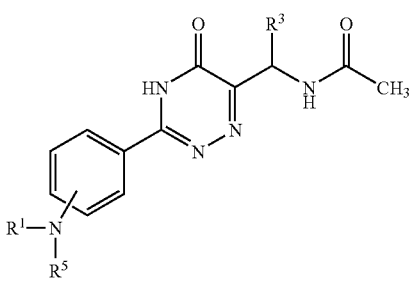

(IXa)

in which

R$^1$, R$^5$ and R$^3$ have the meanings indicated above, can be reacted with an acid.

The reaction can in general be carried out in inert solvents, preferably in a temperature range from 20° C. to 100° C. at normal pressure.

As inert solvents, those suitable for the reduction of (VII) can be used; methanol or ethanol is preferred.

Acids are, for example, trifluoroacetic acid, sulfuric acid, hydrogen chloride, hydrogen bromide and acetic acid or their mixtures, if appropriate with addition of water; hydrogen chloride or hydrogen chloride/water is particularly preferred.

In a further process, for the preparation of the compounds (IX), compounds of the formula (XII),

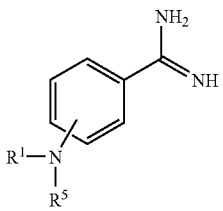

(XII)

or their salts, e.g. hydrochloride or hydrobromide salts, in which R$^1$ and R$^5$ have the meanings indicated above, can be reacted in the first stage with hydrazine, and the reaction product resulting therefrom can be reacted in a second stage with compounds of the formula (XIII),

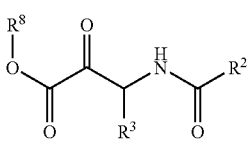

(XIII)

in which

R$^2$ and R$^3$ have the meanings indicated above, and

R$^8$ represents C$_1$–C$_4$-alkyl, preferably methyl or ethyl.

The reaction of the first stage can in general be carried out in inert solvents, preferably in a temperature range from −10° C. to 50° C. at normal pressure (cf., for example, K. M. Doyle, F. Kurzer, *Synthesis* 1974, 583).

The reaction of the second stage can in general be carried out in inert solvents, preferably in a temperature range from 20 to 80° C. at normal pressure.

Inert solvents for the reactions of the first and the second stage are, for example, alcohols such as methanol, ethanol, n-propanol, isopropanol, n-butanol or tert-butanol, amides such as dimethylformamide, alkyl sulfoxides such as dimethyl sulfoxide; methanol or ethanol are preferred.

The compounds (IXa) can be prepared using compounds (XII) and compounds (XIII),
in which $R^2$ represents methyl,
under the same conditions as compounds (IX).

For the preparation of the compounds (XII), compounds of the formula (XIV),

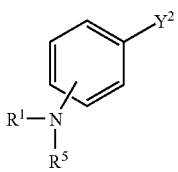

(XIV)

in which
$R^1$ and $R^5$ have the meanings mentioned above and
$Y^2$ represents cyano or methoxycarbonyl, can be reacted—if $Y^2$ represents cyano—with ammonium bromide or chloride and gaseous ammonia at 140° C. to 150° C. in an autoclave, or with lithium bis(trimethylsilyl)amine and hydrogen chloride in diethyl ether (cf. R. T. Boeré, et al., *J. Organomet. Chem.* 1987, 331, 161–167)

or—if $Y^2$ represents methoxycarbonyl—with trimethylaluminum in a hydrocarbon, e.g. hexane and with ammonium chloride.

If $Y^2$ represents methoxycarbonyl, the reaction can in general be carried out in inert solvents, preferably in a temperature range from initially at −20° C. and subsequently at 20° C. to 80° C. at normal pressure (cf., for example, R. S. Garigipati, *Tetrahedron Lett.* 1990, 31, 1969–1972).

As inert solvents, those suitable for processes [A] and [B] can be used, preferably toluene.

The compounds (XIV) are known or can be synthesized from the corresponding starting materials analogously to known processes.

Instead of compounds (XII), it is also possible to employ compounds of the formula (XV),

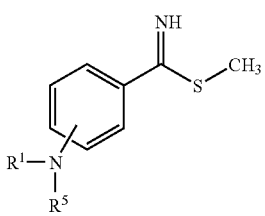

(XV)

in which
$R^1$ and $R^5$ have the meanings indicated above, which can be prepared according to K. M. Doyle, F. Kurzer, *Synthesis* 1974, 583.

The compounds (XV) are known or can be synthesized from the corresponding starting materials analogously to known processes.

For the preparation of the compounds (XIII), compounds of the formula (XVI),

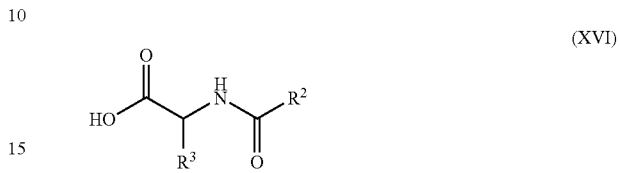

(XVI)

in which
$R^2$ and $R^3$ have the meanings indicated above, can be reacted with compounds of the formula (XVII),

(XVII)

in which
$R^8$ has the meaning indicated above and
$X^2$ represents halogen, preferably chlorine or bromine.

The reaction is in general carried out in inert solvents, if appropriate in the presence of a base and of a catalyst such as dimethylaminopyridine, preferably in a temperature range from 20 to 80° C. at normal pressure (cf., for example, Charles, *J. Chem. Soc., Perkin Trans.* 1, 1980, 1139).

Suitable inert solvents are those mentioned for processes [A] and [B], preferably tetrahydrofuran or diethyl ether.

Suitable bases are those recommended for the analogously to the in processes [A] and [B], preferably pyridine, sodium hydride, potassium tert-butoxide, lithium diisopropylamide, piperidine or triethylamine.

The compounds (XVII) are known or can be synthesized from the corresponding starting materials analogously to known processes.

For the preparation of the compounds (XVI), compounds of the formula (XVIII),

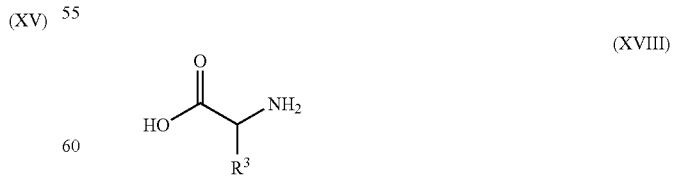

(XVIII)

in which
$R^3$ has the meaning indicated above, can be reacted with compounds of the formula (XIX),

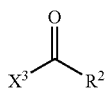

in which
R² has the meaning indicated above and
X³ represents halogen, preferably chlorine or bromine.

The reaction is in general carried out in inert solvents, if appropriate in the presence of a base, if appropriate in the presence of trimethylsilyl chloride, preferably in a temperature range from −10 to 50° C. at normal pressure.

Suitable inert solvents are those mentioned for processes [A] and [B], preferably methylene chloride.

Suitable bases include those recommended for processes [A] and [B], preferably triethylamine, sodium hydroxide or potassium hydroxide in aqueous solution.

The compounds (XVIII) and (XIX) are known or can be synthesized from the corresponding starting materials analogously to known processes.

For the synthesis of intermediates, compounds (I), if appropriate also the methods described in WO 99/24433 and EP-A 1 092 719, are used.

Functional groups are optionally protected during the synthesis using suitable, protective groups, which can subsequently be removed again (cf., for example, T. W. Greene, P. Wuts, "Protective Groups in Organic Synthesis", 2nd ed., Wiley; New York, 1991).

The processes described above can be illustrated by way of example by the following reaction schemes:

Scheme 1:

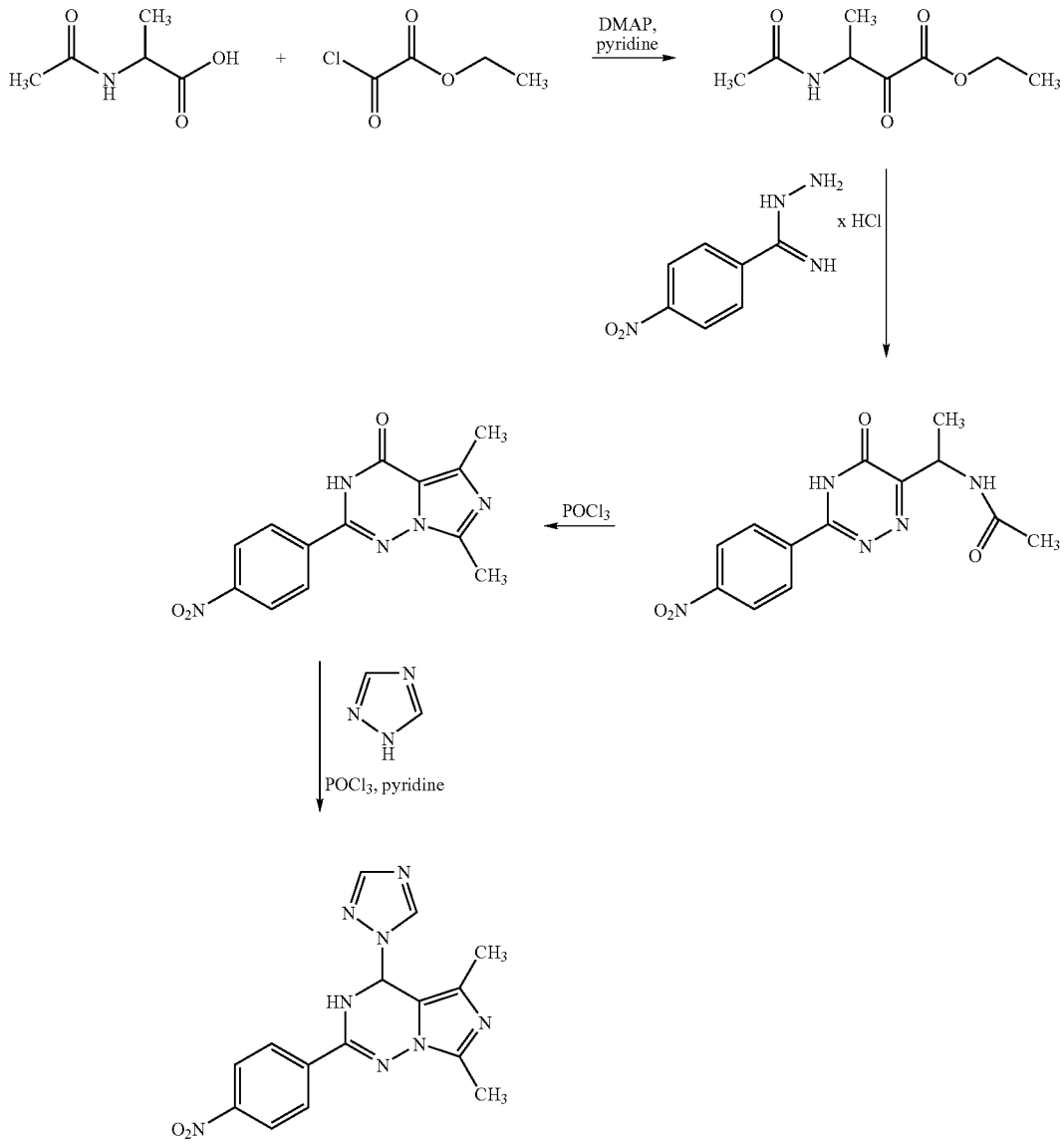

Scheme 2:
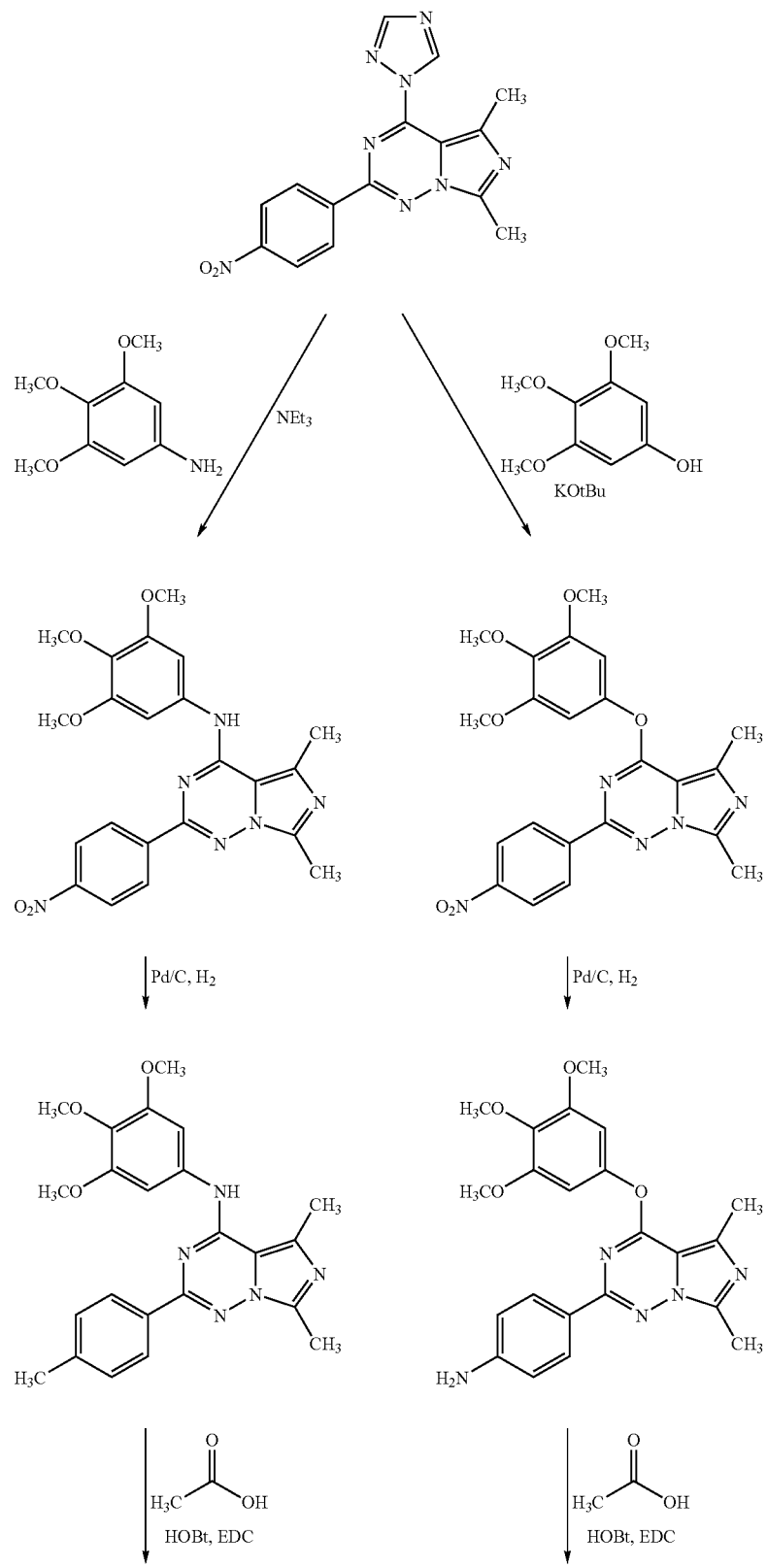

-continued

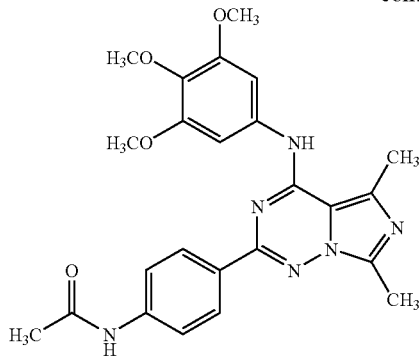
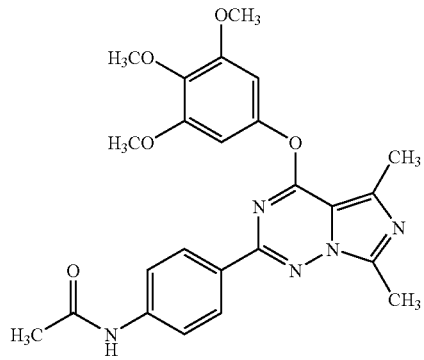

The compounds according to the invention are suitable for use as medicaments in the treatment of humans and animals.

The compounds according to the invention show an unforeseeable, valuable spectrum of pharmacological action. They are distinguished as PDE 10A inhibitors.

It was possible for the first time to show selective PDE 10A inhibition in animal models which makes a connection between PDE 10A inhibitors and Parkinson's disease.

On account of their pharmacological properties, the compounds according to the invention can be used on their own or in combination with other medicaments for the treatment and/or prevention of Parkinson's disease, in particular of idiopathic Parkinson's disease, and of cancers, in particular of tumors, and for the treatment of schizophrenia.

Idiopathic Parkinson's disease is a chronic, progressive neurological disorder, which belongs to a relatively wide classification of neurological diseases which are designated as parkinsonism. It is clinically defined by the occurrence of at least two of the four cardinal symptoms: bradykinesia, resting tremor, muscle stiffness and postural and movement disorders. Pathologically, the idiopathic form of Parkinson's disease is characterized by the loss of pigmented nerve cells, in particular in the area of the *substantia nigra* of the brain. Idiopathic Parkinson's disease makes up about 75% of all parkinsonism diseases. The other 25% of the cases are designated as atypical parkinsonism and include syndromes such as multiple system atrophy, striatonigral degeneration or vascular parkinsonism.

In the context of the present invention, the definition of tumors includes both benign and malignant tumors and thus, for example, also benign neoplasias, dysplasias, hyperplasias, and neoplasias with metastasis formation. Further examples of tumors are carcinomas, sarcomas, carcinosarcomas, tumors of the blood-forming organs, tumors of the nervous tissue, for example of the brain, or tumors of skin cells. In tumor formation, uncontrolled or inadequately controlled cell division occurs. The tumor can be locally restricted, but it can also infiltrate the surrounding tissue and then get lodged by the lymphatic system or by the bloodstream in a new location. There are thus primary and secondary tumors. Primary tumors are originally formed in the organ in which they are found. Secondary tumors have been lodged in another organ by metastasis formation and then spread in their new location.

An abnormal function of the basal ganglia is not only relevant for psychoses, schizophrenia and related schizoaffective disorders, but also plays a role for other neuropsychiatric changes such as depression (Kapur, *Biol. Psychiatr.* 1992, 32, 1–17; Lafer et al., *Psychiatr. Clin. North. Am.* 1997, 20, 855–896) and anxiety disorders (Jetty et al., *Psychiatr. Clin. North. Am.* 2001, 24, 75–97).

Furthermore, the compounds according to the invention are suitable for the treatment of further diseases which can be treated by influencing the cGMP level and/or the cAMP level, such as dementia, stroke, craniocerebral trauma, Alzheimer's disease, dementia with frontal lobe degeneration, Lewy body dementia, vascular dementia, attention deficit syndrome, attention and concentration disorders, affective disorders, psychoses, neuroses, mania or manic depressive disorders, Pick's disease, pain and epilepsy.

The in vitro action of the compounds according to the invention can be shown using the following biological assays:

In Vitro Enzyme Inhibition Tests:

Inhibition of PDE 10A

PDE 10A (WO 01/29 199, FIG. 1A) is expressed recombinantly in full length in Sf9 insect cells (Invitrogen, Carlsbad, Calif.) with the aid of the Bac-to-Bac™ Baculovirus expression system from Life Technologies (Gaithersburg, Md.). 48 h after infection, the cells are harvested and suspended in 20 ml (per 1 l of culture) of lysis buffer (50 mM tris HCl, pH 7.4, 50 mM NaCl, 1 mM $MgCl_2$, 1.5 mM EDTA, 10% glycerol plus 20 µl of Protease Inhibitor Cocktail Set III [CalBiochem, La Jolla, Calif. USA]). The cells are treated with ultrasound at 4° C. for 1 minute and subsequently centrifuged at 10 000 rpm for 30 minutes at 4° C. The supernatant (PDE 10A preparation) was collected and stored at –20° C.

The test substances are dissolved in 100% DMSO for the determination of their in vitro action on PDE 10A and serially diluted. Typically, dilution series from 200 µM to 1.6 µM are prepared (resulting final concentrations in the test: 4 µM to 0.032 µM). 2 µl of the diluted substance solutions in each case are introduced into the hollows of microtiter plates (Isoplate; Wallac Inc., Atlanta, Ga.). Subsequently, 50 µl of a dilution of the PDE 10A preparation described above are added. The dilution of the PDE 10A preparation is chosen such that during the later incubation less than 70% of the substrate is reacted (typical dilution: 1:10 000; dilution buffer: 50 mM tris/HCl pH 7.5, 8.3 mM $MgCl_2$, 1.7 mM EDTA, 0.2% BSA). The substrate, $[5',8-^3H]$ adenosine 3',5'-cyclic phosphate (1 µCi/µl; Amersham Pharmacia Biotech., Piscataway, N.J.) is diluted 1:2000 with assay buffer (50 mM tris/HCl pH 7.5, 8.3 mM $MgCl_2$, 1.7 mM EDTA) to a concentration of 0.0005 µCi/µl. The enzyme reaction is finally started by addition of 50 µl (0.025 µCi) of the diluted substrate. The test batches are incubated for 60 min at 20°

C. and the reaction is stopped by addition of 25 μl of a suspension containing 18 mg/ml of Yttrium Scintillation Proximity Beads (Amersham Pharmacia Biotech., Piscataway, N.J.). The microtiter plates are sealed using a film and allowed to stand for 60 min at 20° C. Subsequently, the plates are measured for 30 s per hollow in a Microbeta scintillation counter (Wallac Inc., Atlanta, Ga.). $IC_{50}$ values are determined by means of graphic plotting of the substance concentration against the percentage inhibition.

The PDE 10A-inhibiting action of the compounds according to the invention may be shown by the following examples:

| Example | $IC_{50}$ [nM] |
|---------|----------------|
| 2       | 37             |
| 9       | 30             |
| 11      | 43             |
| 12      | 8              |
| 13      | 5              |
| 15      | 6              |

Inhibition of the PDEs 1–5, 7–9 and 11

Recombinant PDE 1C (GenBank/EMBL accession number: NM_005020, Loughney et al. *J. Biol. Chem.* 1996 271, 796–806), PDE 2A (GenBank/EMBL accession number: NM_002599, Rosman et al. *Gene* 1997 191, 89–95), PDE3B (GenBank/EMBL accession number: NM_000922, Miki et al. *Genomics* 1996 36, 476–485), PDE 4B (GenBank/EMBL accession number: NM_002600, Obernolte et al. *Gene.* 1993 129, 239–247), PDE 5A (GenBank/EMBL accession number: NM_001083, Loughney et al. *Gene* 1998 216, 139–147), PDE 7B (GenBank/EMBL accession number: NM_018945, Hetman et al. *Proc. Natl. Acad. Sci. U.S.A.* 2000 97, 472–476), PDE 8A (GenBank/EMBL accession number: AF_056490, Fisher et al. *Biochem. Biophys. Res. Commun.* 1998 246, 570–577), PDE 9A (GenBank/EMBL accession number: NM_002606, Fisher et al. *J. Biol. Chem.* 1998 273, 15559–15564), PDE 11A (GenBank/EMBL accession number: NM_016953, Fawcett et al. *Proc. Natl. Acad. Sci* 2000 97, 3702–3707) were expressed in Sf9 cells with the aid of the pFASTBAC Baculovirus expression system (GibcoBRL).

The in vitro action of test substances on recombinant PDE 3B, PDE 4B, PDE 7B, PDE 8A and PDE 11A is determined according to the test protocol described above for PDE 10A. For the determination of a corresponding action on recombinant PDE 1C, PDE 2A, PDE 5A and PDE 9A, the protocol is adapted as follows: In the case of PDE 1C, calmodulin ($10^{-7}$ M) and $CaCl_2$ (3 mM) are additionally added to the reaction batch. PDE 2A is stimulated in the test by addition of cGMP (1 μM) and tested using a BSA concentration of 0.01%. For PDE 5A and PDE 9A, [8-$^3$H] cGMP (Amersham Pharmacia Biotech., Piscataway, N.J.) is employed as a substrate.

The suitability of the compounds according to the invention for the treatment of Parkinson's disease can be shown in the following animal models:

Haloperidol Catalepsy of Rats

The neuroleptic haloperidol is a high-affinity antagonist on the dopamine D2 receptor. In humans and animals, the administration of a relatively high dose of haloperidol causes a transient blockade of dopaminergic neurotransmission. This blockade leads to a disorder of the extrapyramidal motor functions, "catalepsy", in which a given posture is retained for longer than normal. The catalepsy induced in animals by neuroleptics is generally regarded as a model for the hypokinesia and rigidity in Parkinson's patients (Elliott et al., J Neural Transm [P-D Sect] 1990; 2: 79–89). The time which an animal needs in order to change a given position is used as an index for the degree of catalepsy (Sanberg et al., Behav. Neurosci. 1988; 102: 748–59).

In the catalepsy experiments, male rats were divided at random into groups, to which either vehicle or different doses of the compounds to be tested are administered. Each rat receives an intraperitoneal injection of 1.5 mg/kg of haloperidol. The cataleptic behavior of the animals is recorded 120 min after the administration of haloperidol. The compounds to be tested are administered to the rats at such a time interval before the catalepsy test that at the time of the behavior test the maximum plasma concentration is achieved.

For the measurement of the cataleptic behavior, the animal is placed with both forepaws on a block of wood of 9×5.5×5.5 cm height×width×depth. The time which an animal needs in order to take both paws off the block of wood is recorded as the duration of catalepsy. After 180 sec, the animals are taken from the block.

6-Hydroxydopamine (6-OH-DA) Lesion in Rats

The degeneration of the dopaminergic nigrostriatal and striatopallidal neurotransmission is the main sign of Parkinson's disease. The syndrome of Parkinson's disease can be simulated to a large extent in an animal model in which the neurotoxin 6-OH-DA is injected intracerebrally into rats.

For the experiments described, male rats (Harlan Winkelmann, Germany; weight at the start of the experiment: 180–200 g) were kept under controlled conditions (atmospheric humidity, temperature) and a 12 hour light-dark cycle. The animals—provided they are not in an experiment—have free access to water and food.

On the operation day, pargyline (Sigma, St. Louis, Mo., USA; 50 mg/kg i.p.) and desmethylimipramine hydrochloride (Sigma; 25 mg/kg i.p.) are administered to the animals 30 minutes before the lesion in order to suppress the metabolism of 6-hydroxydopamine, or in order to prevent the uptake of 6-hydroxydopamine into noradrenergic structures. After initiating the anesthesia by means of sodium pentobarbital (50 mg/kg i.p.), the experimental animals are fixed in a stereotactic frame. The lesion to the nigrostriatal neurotransmission is carried out by means of a unilateral, single injection of 8 μg of 6-OH-DA hydrobromide (Sigma, St. Louis, Mo., USA), dissolved in 4 μl of a 0.01% strength ascorbic acid-saline solution. The solution is injected slowly (1 μl/min). The coordinates of the injection according to König and Klippel are: 2.4 mm anterior, 1.49 mm lateral, 2.7 mm ventral. After the injection the injection needle was left in situ for another 5 minutes in order to facilitate the diffusion of the neurotoxin.

After the operation, the animals are put onto a warm plate and after waking up under surveillance they are transferred to their cages again, where they received food and water ad libidum.

In the drug group, the animals are treated with substance one day after the operation up to the end of the experiment 28 days after the operation.

Such 6-OHDA-damaged animals are divided into various treatment groups, which receive either vehicle or various doses of the compound to be investigated. For comparison purposes, a group of sham-damaged animals (instead of 6-OHDA 0.9% strength sodium chloride solution in water is injected) is additionally included.

The motor failures resulting from the lesion are quantified using the following tests, as described in the respective literature:

a) Staircase Test (Forepaws Coordination Test):

Barnéoud et al: Effects of complete and partial lesions of the dopaminergic mesotelencephalic system on skilled forelimb use in the rat. *Neuroscience* 1995, 67, 837–848.

b) Accelerating Rotarod Test (Balancing Test):

Spooren et al.: Effects of the prototypical mGlu$_5$ receptor antagonist 2-methyl-6-(phenylethynyl)pyridine on rotarod, locomotor activity and rotational responses in unilateral 6-OHDA-lesioned rats. *Eur. J. Pharmacol.* 2000, 406, 403–410.

c) Forepaws Tractive Force Measurement:

Dunnet et al.: A laterized grip strength test to evaluate unilateral nigrostriatal lesions in rats. *Neurosci. Lett.* 1998, 246, 1–4.

The suitability of the compounds according to the invention for the treatment of schizophrenia can be shown in the following animal models:

Catalepsy Test on Rats

The action of test substances on the function of the basal ganglia can be investigated in an animal model using the "catalepsy test on rats" (Sanberg et al., *Behav. Neurosci.* 1988, 102, 748–759). Catalepsy is remaining in a certain body position, accompanied by increased muscle tone. If a normal animal is brought into an unusual position, it changes its body posture within a few seconds, but a cataleptic animal remains for a relatively long time in the imposed posture. The period of time which elapses up to the correction of an imposed position can be used as a measure of the intensity of catalepsy. In a sufficiently high dose, the antipsychotic haloperidol also induces cataleptic behavior (e.g. Chartoff et al., *J. Pharmacol. Exp. Therap.* 291, 531–537). In EP-A 1 250 923, it is described that the selective PDE10 inhibitor papaverine induces a potentiation of haloperidol catalepsy.

The action of the selective PDE10 inhibitors is investigated in the animal model mentioned. A low dose of haloperidol (0.3 mg/kg s.c.) is given on its own 30 min before the catalepsy test or administered together with the compound. In order to measure the cataleptic behavior, both forepaws of the rat are put onto a block of wood of 9 cm height and 5.5 cm width×5.5 cm depth. The time which elapses until an animal pulls its forepaws down from the block again is recorded as the duration of catalepsy. All rats are taken from the block of wood after 60 seconds at the latest. The data acquired from each treatment group (10 animals in each case) are analyzed statistically by means of variance analysis (ANOVA).

The new active compounds can be converted in a known manner into the customary formulations, such as tablets, coated tablets, pills, granules, aerosols, syrups, emulsions, suspensions and solutions, using inert, nontoxic, pharmaceutically suitable vehicles or solvents. Here, the therapeutically active compound should in each case be present in a concentration of approximately 0.5 to 90% by weight of the total mixture, i.e. in amounts which are sufficient in order to achieve the dose range indicated.

The formulations are produced, for example, by extending the active compounds using solvents and/or vehicles, if appropriate using emulsifiers and/or dispersants, where, for example, in the case of the use of water as a diluent, organic solvents can optionally be used as auxiliary solvents.

Administration is carried out in the customary manner, preferably orally, transdermally or parenterally, in particular perlingually or intravenously. It can, however, also be carried out by inhalation via the mouth or nose, for example with the aid of a spray, or topically via the skin.

In general, it has proven advantageous to administer amounts of approximately 0.001 to 10, in the case of oral administration preferably approximately 0.005 to 3, mg/kg of body weight, to achieve effective results.

In spite of this, it may optionally be necessary to depart from the amounts mentioned, namely depending on the body weight or on the type of administration route, on individual behavior toward the medicament, the manner of its formulation and the time or interval at which administration takes place. Thus, in some cases it can be adequate to manage with less than the aforementioned minimum amount, while in other cases the upper limit mentioned must be exceeded. In the case of the administration of relatively large amounts, it may be advisable to divide these into a number of individual doses over the course of the day.

If not stated otherwise, all quantitative data relate to percentages by weight. Solvent ratios, dilution ratios and concentration data of liquid/liquid solutions in each case relate to the volume. The statement "w/v" means "weight/volume". For instance, "10% w/v": 100 ml of solution or suspension contain 10 g of substance.

Abbreviations:

abs. absolute
aq. aqueous
BINAP 2,2'-bis(diphenylphosphino)-1,1'-binaphthalene
Bn benzyl
Boc tert-butoxycarbonyl
BSA bovine serum albumin
cGMP cyclic guanosine-3',5'-monophosphate
CDI N,N'-carbonyldiimidazole
CH cyclohexane
DBU 1,8-diazabicyclo[5.4.0]undec-7-ene
TLC thin-layer chromatography
DCI direct chemical ionization (in MS)
DCM dichloromethane
DIC diisopropylcarbodiimide
DIEA N,N-diisopropylethylamine
DMA N,N-dimethylacetamide
DMAP 4-N,N-dimethylaminopyridine
DMF N,N-dimethylformamide
DMSO dimethyl sulfoxide
EDC N'-(3-dimethylaminopropyl)-N-ethylcarbodiimide× HCl
EDTA ethylenediamine tetra-acetic acid
EA ethyl acetate (acetic acid ethyl ester)
EI electron impact ionization (in MS)
Eq equivalent(s)
ESI electrospray ionization (in MS)
M.p. melting point
sat. saturated
HATU O-(7-azabenzotriazol-1-yl)-N,N,N',N'-tetramethyluronium hexafluorophosphate
HBTU O-(benzotriazol-1-yl)-N,N,N',N'-tetramethyluronium hexafluorophosphate
HOBt 1-hydroxyl-1H-benzotriazole×H$_2$O
HPLC High-pressure, high-performance liquid chromatography
Conc. concentrated
B.p. boiling point
LC-MS liquid chromatography-coupled mass spectroscopy
LDA lithium N,N-diisopropylamide Lit. literature (reference)
Soln. solution
MW molecular weight
MS mass spectroscopy
NMR nuclear magnetic resonance spectroscopy
PyBOP benzotriazol-1-yloxytris(pyrrolidino)phosphonium hexafluorophosphate
RF reflux
$R_f$ retention index (in TLC)
RP reverse phase (in HPLC)
RT 20° C.
$R_t$ retention time (in HPLC)
TBTU O-(benzotriazol-1-yl)-N,N,N',N'-tetramethyluronium tetrafluoroborate
TEA triethylamine
TFA trifluoroacetic acid
THF tetrahydrofuran
TRIS tris(hydroxymethyl)aminomethane
v/v volume-to-volume ratio (of a solution)
dil. diluted
aq. aqueous
dec. decomposition HPLC and LC-MS Methods:

Method 1 (HPLC)
Instrument: HP 1100 with DAD detection; column: Kromasil RP-18, 60 mm×2 mm, 3.5 μm; eluent: A=5 ml HClO$_4$/l H$_2$O, B=acetonitrile; gradient: 0 min 2% B, 0.5 min 2% B, 4.5 min 90% B, 6.5 min 90% B; flow: 0.75 mmin; temp.: 30° C.; detection UV 210 mn.

Method 2 (LC-MS)
Instrument: Micromass Quattro LCZ, HP1100; column: Symmetry C18, 50 mm×2.1 mm, 3.5 μm; eluent A: water+0.05% formic acid, eluent B: acetonitrile+0.05% formic acid; gradient: 0.0 min 90% A→4.0 min 10% A→6.0 min 10% A; oven: 40° C.; flow: 0.5 ml/min; UV detection: 210 nm.

Method 3 (LC-MS)
Instrument: Micromass Platform LCZ, HP 1100; column: Symmetry C18, 50 mm×2.1 mm, 3.5 μm; eluent A: water+0.05% formic acid, eluent B: acetonitrile+0.05% formic acid; gradient: 0.0 min 90% A→4.0 min 10% A→6.0 min 10% A; oven: 40° C.; flow: 0.5 ml/min; UV detection: 210 nm.

Starting Compounds

EXAMPLE 1A

4-Nitrobenzenecarboximidamide hydrochloride

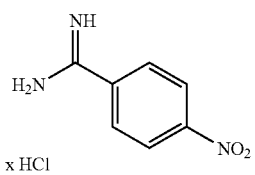

21.40 g (400 mmol) of ammonium chloride are suspended in 200 ml of anhydrous toluene under an argon atmosphere in a three-necked flask having a thermometer, condenser, dropping funnel and mechanical stirrer and cooled to 0° C. 400 mmol of trimethylaluminum (200 ml of 2 M solution in hexane) are added dropwise, and the mixture is stirred at 20° C. until evolution of gas is no longer observed (about 2 hours). 19.75 g (133 mmol) of 4-nitrobenzonitrile are subsequently added to the mixture and the reaction mixture is stirred overnight at 80° C.

After cooling to 0° C., the mixture is treated dropwise with 250 ml of methanol and stirred vigorously at 20° C. The reaction mixture is filtered and the residue is washed well with methanol. The filtrate is concentrated, and the residue is suspended using dichloromethane/methanol 10/1. The insoluble solid consisting of ammonium chloride is filtered off with suction, the filtrate is concentrated again and the product is obtained as a solid.

Total yield: 19.53 g (73 of theory)
MS (DCI): m/z=183 (M+NH$_4$—HCl)$^+$.

EXAMPLE 2A

3-Nitrobenzenecarboximidamide hydrochloride

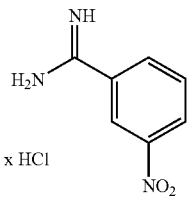

7.22 g (135 mmol) of ammonium chloride are reacted analogously to example 1A with 135 mmol of trimethylaluminum (67.5 ml of 2 M solution in hexane) and 10 g (67.51 mmol) of 3-nitrobenzonitrile.

Total yield: 9.7 g (71% of theory)
HPLC (method 1): $R_t$=1.57 min.
MS (ESIpos): m/z=166 (M+H—HCl)$^+$.

EXAMPLE 3A

4-Bromobenzenecarboximidamide hydrobromide

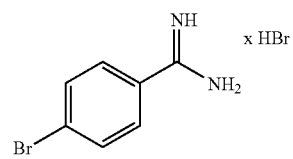

4-Bromobenzonitrile (36.4 g, 0.2 mol), ammonium bromide (39.2 g, 0.4 mol) and ammonia gas (34.0 g, 2 mol) are heated under autogenous pressure in an autoclave for 9 h at 140–150° C. The autoclave contents are concentrated and extracted by stirring with ethanol. The residue is filtered off and again extracted by stirring with ethanol. The extracts are combined and concentrated to about 100 ml. The precipitated solid is filtered off with suction, washed with ethanol and dried.

Yield 21.4 g (38% of theory)
$^1$H-NMR (400 MHz, DMSO-d$_6$): δ=7.75 (d, 2H), 7.87 (d, 2H) 9.10 (s, 3H).

EXAMPLE 4A

Ethyl 3-(acetylamino)-2-oxobutanoate

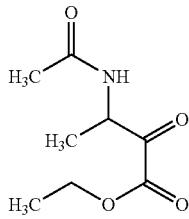

N-Acetylalanine (4.92 g, 37.5 mmol), 9.10 ml of pyridine and 150 mg of DMAP are dissolved in 200 ml THF, and the solution is brought to boiling. At boiling heat, 8.6 ml (10.5 g, 75 mmol) of ethyl oxalyl chloride are added dropwise; after addition is complete the mixture is stirred for a further 3 h at boiling heat. After cooling, the reaction mixture is added to 600 ml of ice water, extracted with ethyl acetate (4×150 ml) and the combined organic phases are washed with 200 ml of sat. sodium chloride solution, dried over sodium sulfate and concentrated. The material obtained is dissolved in ethanol without delay and reacted further.

EXAMPLE 5A

N-{1-[3-(4-Nitrophenyl)-5-oxo-4,5-dihydro-1,2,4-triazin-6-yl]ethyl}acetamide

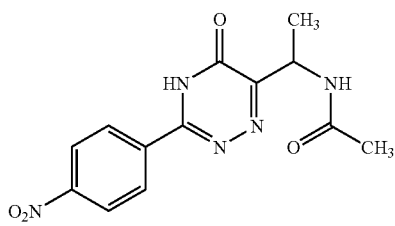

7.30 g (7.09 ml, 145.82 mmol) of hydrazine hydrate are added dropwise to 24.50 g (121.5 mmol) of 4-nitrobenzenecarboximidamide hydrochloride from example 1A are in 250 ml of ethanol. The mixture is stirred for one hour at 20° C. After this time, 34.12 g (182.28 mmol) of ethyl 3-(acetylamino)-2-oxobutanoate from example 4A are added in ethanol, and the reaction mixture is stirred for 4 h at a bath temperature of 70–80° C., subsequently for 12 h at 20° C. The mixture is concentrated and the residue is purified by flash chromatography (eluent: ethyl acetate, subsequently dichloromethane/methanol 30:1).

Yield: 14.80 g (40% of theory).

HPLC (method 1): $R_f$=3.11 min.

MS (ESIpos): m/z=304 (M+H)$^+$.

$^1$H-NMR (400 MHz, MeOH-d$_4$): δ=1.49 (d, 3H), 1.99 (s, 3H), 5.23 (q, 1H), 8.26 (d, 2H), 8.41 (d, 2H) the two NHs cannot be seen.

EXAMPLE 6A

N-{1-[3-(3-Nitrophenyl)-5-oxo-4,5-dihydro-1,2,4-triazin-6-yl]ethyl}acetamide

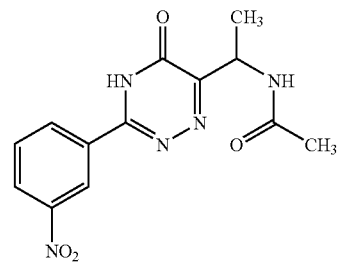

2.89 g (2.81 ml, 57.73 mmol) of hydrazine hydrate are added dropwise to 9.70 g (48.11 mmol) of 3-nitrobenzenecarboximidamide hydrochloride from example 2A in 200 ml of ethanol. The mixture is stirred for one hour at 20° C. After this time, 13.51 g (72.17 mmol) of ethyl 3-(acetylamino)-2-oxobutanoate from example 4A are added in ethanol, and the reaction mixture is stirred for 4 h at a bath temperature of 70–80° C., subsequently for 12 h at 20° C. The mixture is concentrated and the residue is purified by flash chromatography (eluent: ethyl acetate, subsequently dichloromethane/methanol 30:1).

Yield: 1.93 g (13% of theory).

HPLC (method 1): $R_f$=3.07 min.

MS (ESIpos): m/z=304 (M+H)$^+$.

$^1$H-NMR (300 MHz, MeOH-d$_4$): δ=1.49 (d, 3H), 1.99 (s, 3H), 5.21 (q, 1H), 7.81 (t, 1H), 8.42 (d, 1H), 8.52 (d, 1H), 8.93 (s, 1H) both NHs cannot be seen.

EXAMPLE 7A

N-{1-[3-(4-Bromophenyl)-5-oxo-4,5-dihydro-1,2,4-triazin-6-yl]ethyl}acetamide

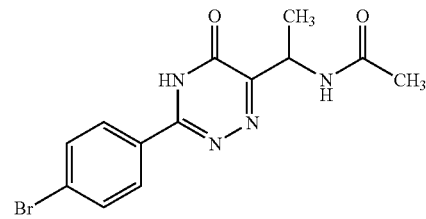

3.50 ml of hydrazine hydrate (3.60 g, 27.5 mmol) are added to 4-bromobenzenecarboximidamide hydrobromide from example 3A (11.8 g) in 150 ml of ethanol, and the mixture is stirred for 1 h. After this time, ethyl 3-(acetylamino)-2-oxobutanoate from example 4A (16.8 g) in 76 ml of ethanol is added dropwise and the reaction mixture is stirred for 3 h at a bath temperature of 80° C., subsequently overnight at 20° C. The mixture is concentrated and the residue is purified by flash chromatography (eluent: dichloromethane/methanol 95:5).

Yield: 4.58 g (15% of theory)

MS (ESI): m/z=337 (M+H)$^+$.

$^1$H-NMR (200 MHz, CDCl$_3$): δ=1.54 (d, 3H), 2.07 (s, 3H), 5.26–5.41 (m, 1H), 7.51 (br. s, 1H), 7.66 (d, 2H), 8.12 (d, 2H).

EXAMPLE 8A 5,7-Dimethyl-2-(4-nitrophenyl)imidazo[5,1-f][1,2,4]triazin-4(3H)-one

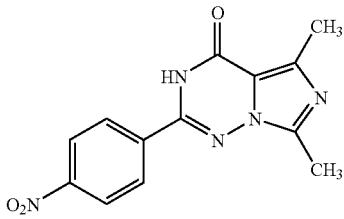

A solution of 13.76 g (8.13 mmol) of N-{1-[3-(4-nitrophenyl)-5-oxo-4,5-dihydro-1,2,4-triazin-6-yl]ethyl}acetamide from example 5A in 150 ml of 1,2-dichloroethane is treated with 20.87 g (12.69 ml, 136.11 mmol) of phosphoryl chloride while cooling with an ice bath. The mixture is stirred for 4 h at 65° C. After cooling, it is hydrolyzed using aqueous sodium hydrogencarbonate solution. The solvent of the organic phase is removed in vacuo and the residue is purified by flash chromatography (eluent gradient:dichloromethane/methanol 200:1-100:1-50:1).

Yield: 10.6 g (82% of theory)

MS (ESI): m/z=286 (M+H)$^+$.

$^1$H-NMR (300 MHz, MeOH-d$_4$): δ=2.61 (s, 3H), 2.66 (s, 3H), 8.22 (d, 2H), 8.42 (d, 2H).

EXAMPLE 9A 5,7-Dimethyl-2-(3-nitrophenyl)imidazo[5,1-f][1,2,4]triazin-4-(3H)one

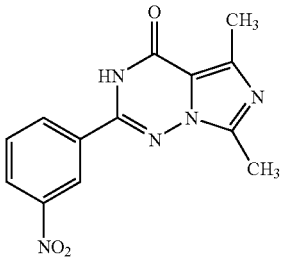

A solution of 1.93 g (6.36 mmol) of N-{1-[3-(3-nitrophenyl)-5-oxo-4,5-dihydro-1,2,4-triazin-6-yl]ethyl}acetamide from example 6A in 1,2-dichloroethane is treated with 2.93 g (1.78 ml, 19.09 mmol) of phosphoryl chloride. The mixture is stirred for 3 h at 95° C. After cooling, it is hydrolyzed using a couple of drops of aqueous sodium hydrogencarbonate solution. The solvent is removed in vacuo and the residue is purified by flash chromatography (eluent gradient: dichloromethane/methanol 100:1-50:1-30:1-20:1).

Yield: 1.46 g (80% of theory)

HPLC (method 1): R$_t$=3.47 min.

MS (ESI): m/z=286 (M+H)$^+$.

EXAMPLE 10A 2-(4-Bromophenyl)-5,7-dimethylimidazo[5,1-f][1,2,4]triazin4-(3H)one

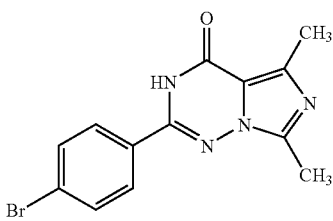

A solution of 10.0 g (29.66 mmol) of N-{1-[3-(4-bromophenyl)-5-oxo-4,5-dihydro-1,2,4-triazin-6-yl]ethyl} from example 7A in 340 ml of 1,2-dichloroethane is treated with 13.64 g (8.30 ml, 88.98 mmol) of phosphoryl chloride. The mixture is boiled under reflux for 15 h. After cooling, the solvent is removed. The residue is stirred with diethyl ether and filtered off with suction. The crystals are stirred for 1 h with 150 ml of saturated aqueous sodium hydrogencarbonate solution, and subsequently diluted with 100 ml of water. After 30 min, the solid is filtered off with suction, washed well with water and rewashed with petroleum ether.

Yield: 9.30 g (98% of theory)

MS (ESI): m/z=319 (M+H)$^+$

HPLC (method 1): R$_t$=3.79 min.

$^1$H-NMR (300 MHz, DMSO-d$_6$): δ=2.63 (s, 3H), 2.75 (s, 3H), 7.82 (d, 2H), 7.97 (d, 2H), 12.43 (br. s, 1H).

EXAMPLE 11A 5,7-Dimethyl-2-(4-nitrophenyl)-4-(1H-1,2,4-triazol-1-yl)imidazo[5,1-f][1,2,4]triazine

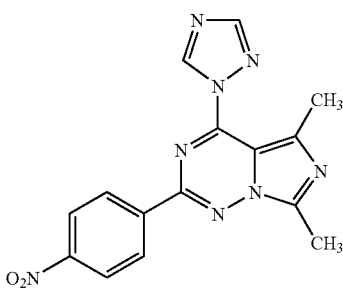

2.53 g (1.54 ml, 16.51 mmol) of phosphoryl chloride are added dropwise under argon to a solution of 1.57 g (5.50 mmol) of 5,7-dimethyl-2-(4-nitrophenyl)imidazo-[5,1-f][1,2,4]triazin-4-(3H)one from example 8A in 10 ml of dry pyridine at 0° C., and the mixture is stirred for 30 min at 20° C. Subsequently, 3.42 g (49.53 mmol) of 1,2,4-triazole are added, and the mixture is stirred overnight at RT. The reaction mixture is concentrated, the residue is treated with aqueous sodium hydrogencarbonate solution, and the mixture is extracted using dichloromethane. The organic phase is dried (sodium sulfate) and the solvent is removed in vacuo. The residue is purified by flash chromatography (eluent: dichloromethane/methanol 100:1).

Yield: 1.06 g (57% of theory)

MS (ESI): m/z=337 (M+H)$^+$

EXAMPLE 12A 5,7-Dimethyl-2-(3-nitrophenyl)-4-(1H-1,2,4-triazol-1-yl)imidazo[5,1-f][1,2,4]triazine

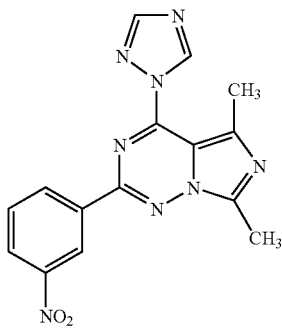

2.35 g (15.35 mmol) of phosphoryl chloride are added dropwise under argon to a solution of 1.46 g (5.12 mmol) of 5,7-dimethyl-2-(3-nitrophenyl)imidazo-[5,1-f][1,2,4]triazin-4-(3H)one from example 9A in 50 ml of dry pyridine at 0° C. and the mixture is stirred for 30 min at RT. Subsequently, 3.18 g (46.06 mmol) of 1,2,4-triazole are added, and the mixture is stirred for 3 h at 20° C. The reaction mixture is concentrated, the residue is treated with aqueous sodium hydrogencarbonate solution and the mixture is extracted with dichloromethane. The organic phase is dried (sodium sulfate) and the solvent is removed in vacuo. The residue is purified by flash chromatography (eluent: dichloromethane/methanol 100:1).

Yield: 0.736 g (43% of theory)

MS (ESI): m/z=337 (M+H)+

HPLC (method 1): $R_t$=3.96 min.

$^1$H-NMR (200 MHz, CDCl$_3$): δ=2.86 (s, 3H), 2.92 (s, 3H), 7.73 (t, 1H), 8.30 (s, 1H), 8.40 (d, 1H), 8.73 (d, 1H), 9.21 (s, 1H), 9.43 (s, 1H).

EXAMPLE 13A 2-(4-Bromophenyl)-5,7-dimethyl-4-(1H-1,2,4-triazol-1-yl)imidazo[5,1-f][1,2,4]triazine

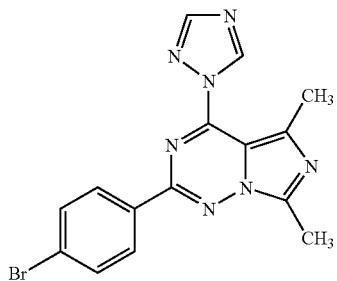

11.53 g (7.0 ml, 75.20 mmol) of phosphoryl chloride are added dropwise under argon to a solution of 8.00 g (25.07 mmol) of 2-(4-bromophenyl)-5,7-dimethylimidazo-[5,1-f][1,2,4]triazin-4-(3H)one from example 10A in 250 ml of dry pyridine at 0° C. and the mixture is stirred for 30 min at RT. Subsequently, 15.58 g (225.59 mmol) of 1,2,4-triazole are added, and the mixture is stirred overnight at 20° C. The reaction mixture is concentrated, the residue is treated with aqueous sodium hydrogencarbonate solution and the mixture is extracted with dichloromethane. The organic phase is dried (sodium sulfate) and the solvent is removed in vacuo. The residue is purified by flash chromatography (eluent: dichloromethane/methanol 100:1).

Yield: 7.98 g (86% of theory)

MS (DCI/NH$_3$): m/z=370 (M+H)+

$^1$H-NMR (200 MHz, MeOH-d$_4$): δ=2.89 (s, 3H), 2.96 (s, 3H), 7.82 (d, 2H), 8.46 (d, 2H), 8.52 (s, 1H), 9.83 (s, 1H).

EXAMPLE 14A 5,7-Dimethyl-2-(4-nitrophenyl)-4-(3,4,5-trimethoxyphenoxy)imidazo[5,1-f][1,2,4]triazine

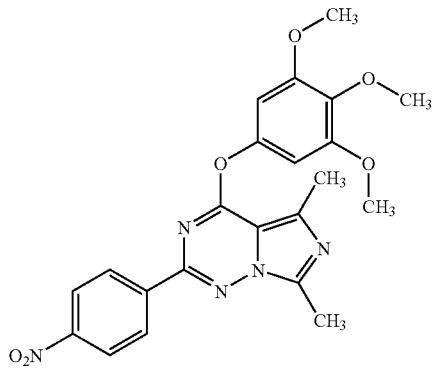

A solution of 40 mg (0.33 mmol) of potassium tert-butoxide and 60 mg (0.33 mmol) of 3,4,5-trimethoxyphenol in 50 ml of tetrahydrofuran is stirred for 30 min. 70 mg (0.22 mmol) of 5,7-dimethyl-2-(4-nitrophenyl)-4-(1H-1,2,4-triazol-1-yl)imidazo-[5,1-f][1,2,4]triazine from example 11A are added thereto and the mixture is heated for 3 h at 70° C. After cooling, the solvent is removed and the residue is purified by chromatography (eluent gradient: dichloromethane/methanol 200:1-100:1).

Yield: 76 mg (75% of theory)

MS (ESI): m/z=452 (M+H)+

HPLC (method 1): $R_t$=4.29 min.

$^1$H-NMR (300 MHz, CDCl$_3$): δ=2.75 (s, 3H), 2.79 (s, 3H), 3.88 (s, 6H), 3.92 (s, 3H), 6.59 (s, 2H), 8.25 (d, 2H), 8.33 (d, 2H).

EXAMPLE 15A 5,7-Dimethyl-2-(3-nitrophenyl)-4-(3,4,5-trimethoxyphenoxy)imidazo[5,1-f][1,2,4]triazine

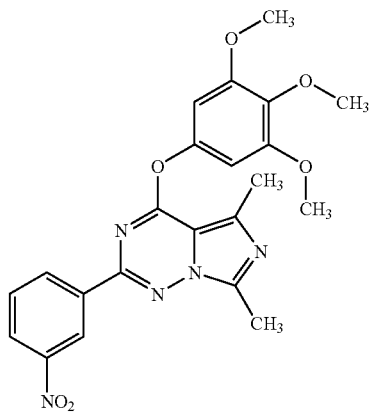

A solution of 175.17 mg (1.04 mmol) of potassium tert-butoxide and 287.53 mg (1.56 mmol) of 3,4,5-trimethoxyphenol in 20 ml of tetrahydrofuran is stirred for 30 min. 350 mg (1.04 mmol) of 5,7-dimethyl-2-(3-nitrophenyl)-4-(1H-1,2,4-triazol-1-yl)imidazo[5,1-f][1,2,4]triazine from example 12A are added thereto and the mixture is heated for 2 h to 70° C. After cooling, the solvent is removed and the residue is taken up and extracted with dichloromethane and 1N sodium hydroxide solution. The organic phase is separated off, dried and the crude product is purified by flash chromatography. (Eluent: dichloromethane/methanol 100:1).

Yield: 403 mg (86% of theory)

MS (ESI): m/z=452 (M+H)$^+$

HPLC (method 1): R$_t$=4.29 min.

$^1$H-NMR (300 MHz, CDCl$_3$): δ=2.76 (s, 3H), 2.80 (s, 3H), 3.90 (s, 6H), 3.93 (s, 3H), 6.63 (s, 2H), 7.59 (t, 1H), 8.28 (d, 1H), 8.47 (d, 1H), 9.00 (s, 1H).

EXAMPLE 16A 2-(4-Bromophenyl)-5,7-dimethyl-4-(3,4,5-trimethoxyphenoxy)imidazo[5,1f][1,2,4]-triazine

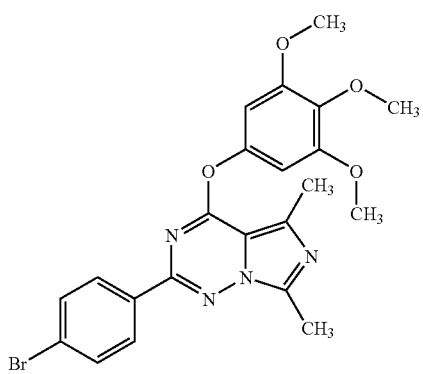

A solution of 1.82 g (16.21 mmol) of potassium tert-butoxide and 2.99 g (16.21 mmol) of 3,4,5-trimethoxyphenol in 100 ml of tetrahydrofuran is stirred for 30 min. 4.0 g (10.80 mmol) of 2-(4-bromophenyl)-5,7-dimethyl-4-(1H-1,2,4-triazol-1-yl)imidazo[5,1-f][1,2,4]triazine from example 13A are added thereto and the mixture is heated for 3 h to 70° C. After cooling, the solvent is removed and the residue is taken up and extracted with dichloromethane and 1N sodium hydroxide solution. The organic phase is separated off, dried and the crude product is purified by flash chromatography. (Eluent: dichloromethane/methanol 200:1-100:1).

Yield: 5.20 g (99% of theory)

MS (ESI): m/z=485 (M+H)$^+$

HPLC (method 1): R$_t$=4.59 min.

$^1$H-NMR (300 MHz, CDCl$_3$): δ=2.73 (s, 3H), 2.75 (s, 3H), 3.87 (s, 6H), 3.91 (s, 3H), 6.59 (s, 2H), 7.53 (d, 2H), 8.02 (d, 2H).

EXAMPLE 17A 5,7-Dimethyl-2-(4-nitrophenyl)-N-(3,4,5-trimethoxyphenyl)imidazo[5,1-f][1,2,4]triazin-4-amine

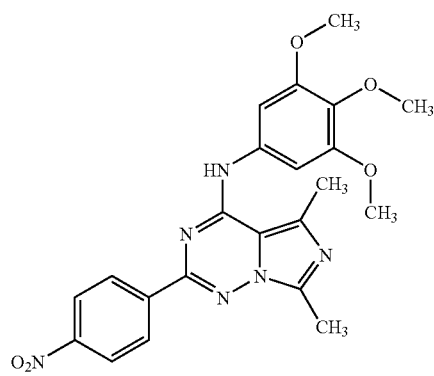

A solution of 130 mg (0.39 mmol) of 5,7-dimethyl-2-(4-nitrophenyl)-4-(1H-1,2,4-triazol-1-yl)imidazo[5,1-f][1,2,4]triazine from example 11A in DMF is treated with 111 mg (0.58 mmol) of 3,4,5-trimethoxyaniline and 80 mg (0.58 mmol) of potassium carbonate. The reaction mixture is stirred overnight at 90° C. After cooling, the solvent is removed on a rotary evaporator, the residue is treated twice more with toluene and the solvent is removed in vacuo again. The product is extracted by stirring with a little methanol and filtered off with suction.

Yield: 128 mg (74% of theory)

MS (ESI): m/z=451 (M+H)$^+$

HPLC (method 1): R$_t$=4.31 min.

$^1$H-NMR (300 MHz, CDCl$_3$): δ=2.74 (s, 3H), 2.80 (s, 3H), 3.90 (s, 3H), 3.94 (s, 6H), 6.59 (s, 2H), 7.07 (s, 2H), 7.13 (br. s, 1H), 8.29 (d, 2H), 8.52 (d, 2H).

EXAMPLE 18A 5,7-Dimethyl-2-(3-nitrophenyl)-N-(3,4,5-trimethoxyphenyl)imidazo[5,1-f][1,2,4]triazin-4-amine

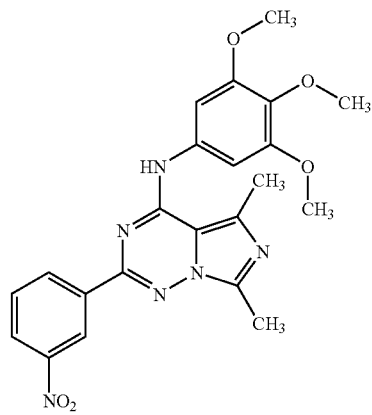

To a solution of 350 mg (1.04 mmol) of 5,7-dimethyl-2-(3-nitrophenyl)-4-(1H-1,2,4-triazol-1-yl)imidazo[5,1-f][1,2,4]triazine from example 12A in DMF is treated with 290 mg (1.56 mmol) of 3,4,5-trimethoxyaniline and 220 mg (1.56 mmol) of potassium carbonate. The reaction mixture is stirred overnight at 90° C. After cooling, the solvent is removed on a rotary evaporator, the residue is treated twice more with toluene and the solvent is removed in vacuo. The product is extracted by stirring with a little methanol and filtered off with suction.

Yield: 342 mg (73% of theory)

MS (ESI): m/z=451 (M+H)$^+$

HPLC (method 1): $R_t$=4.36 min.

$^1$H-NMR (300 MHz, CDCl$_3$): δ=2.76 (s, 3H), 2.82 (s, 3H), 3.90 (s, 3H), 3.9 (s, 6H), 7.08 (s, 2H), 7.16 (br. s, 1H), 7.63 (t, 1H), 8.32 (d, 1H), 8.68 (d, 1H), 9.14 (s, 1H).

EXAMPLE 19A

N-[2-(4-Bromophenyl)-5,7-dimethylimidazo[5,1-f][1,2,4]triazin-4-yl]-N-(3,4,5-tri-methoxyphenyl)amine

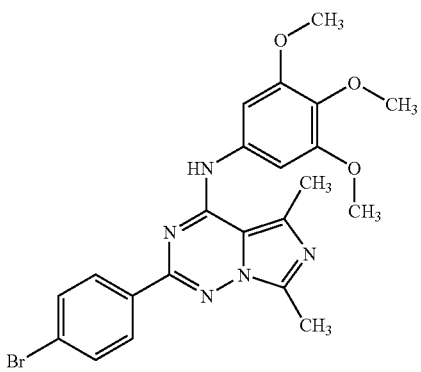

A solution of 4.0 g (10.80 mmol) of 2-(4-bromophenyl)-5,7-dimethyl-4-(1H-1,2,4-triazol-1-yl)imidazo[5,1-f][1,2,4]triazine from example 13A in DMF is treated with 2.97 g (16.21 mmol) of 3,4,5-trimethoxyaniline and 2.24 g (16.21 mmol) of potassium carbonate. The reaction mixture is stirred overnight at 90° C. After cooling, the solvent is removed on a rotary evaporator, the residue is treated twice more with toluene and the toluene is stripped off again. The crude product is extracted by stirring with a little methanol and filtered off with suction.

Yield: 3.60 g (69% of theory)

MS (ESI): m/z=484 (M+H)$^+$

HPLC (method 1): $R_t$=4.61 min.

$^1$H-NMR (300 MHz, CDCl$_3$): δ=2.71 (s, 3H), 2.78 (s, 3H), 3.89 (s, 3H), 3.93 (s, 6H), 7.06 (br. s, 1H), 7.09 (s, 2H), 7.56 (d, 2H), 8.22 (d, 2H).

EXAMPLE 20A

N-2-tert-Butoxycarbonyl-N-1-(4-{5,7-dimethyl-4-[(3,4,5-trimethoxyphenyl)amino]-imidazo[5,1-f][1,2,4]triazin-2-yl}phenyl)glycinamide

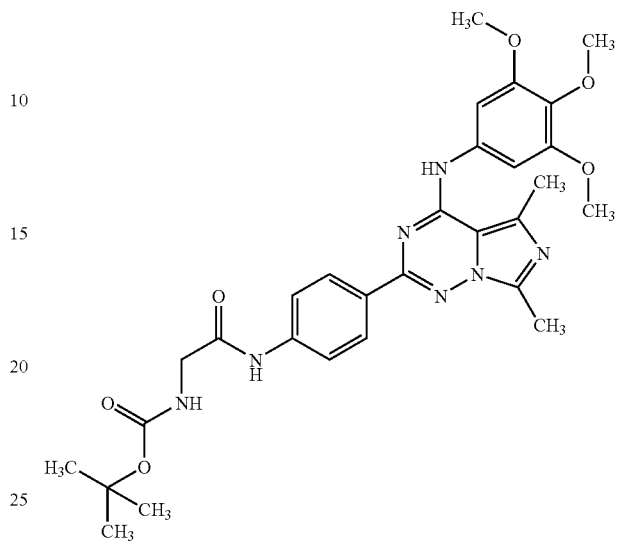

A solution of 46 mg (0.26 mmol) of BOC-glycine in dichloromethane is treated with 35 mg (0.26 mmol) of HOBt and 72 mg (0.71 mmol) of 4-methylmorpholine. The mixture is cooled to −20° C. and treated with 50 mg (0.26 mmol) of EDC. It is stirred for 30 min with warming to RT. Subsequently, 100 mg (0.24 mmol) of N-[2-(4-aminophenyl)-5,7-dimethylimidazo[5,1-f][1,2,4]triazin-4-yl]-N-(3,4,5-trimethoxyphenyl)amine from example 3 are added thereto at −20° C. The mixture is stirred for 24 h at 20° C. To complete the reaction, the total amount of starting materials—excluding the compound of example 3—is added thereto again and the mixture is stirred for a further 24 h. The solvent is removed in vacuo and the residue is purified by means of HPLC.

Yield: 41 mg (30% of theory)

MS (ESI): m/z=578 (M+H)$^+$

PREPARATION EXAMPLES

Example 1

4-[5,7-Dimethyl-4-(3,4,5-trimethoxyphenoxy)imidazo[5,1-f][1,2,4]triazin-2-yl]-aniline

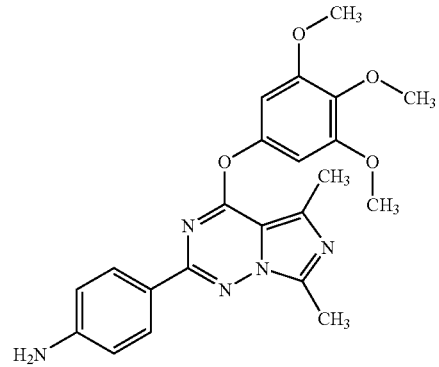

70 mg (0.17 mmol) of 5,7-dimethyl-2-(4-nitrophenyl)-4-(3,4,5-trimethoxyphenoxy)-imidazo[5,1-f][1,2,4]triazine from example 14A are dissolved in methanol under argon. The mixture is treated with 20 mg of palladium on carbon (10% strength). It is hydrogenated for 5 h at a hydrogen pressure of 3 bar. The catalyst is then filtered off from the reaction mixture and the filtrate is concentrated under reduced pressure. The residue is purified by chromatography. (Eluent:dichloromethane/methanol 80:1).

Yield: 65 mg (93% of theory)

MS (ESI): m/z=422 (M+H)$^+$

HPLC (method 1): $R_t$=3.79 min.

$^1$H-NMR (300 MHz, MeOH-d$_4$): δ=2.66 (s, 3H), 2.67 (s, 3H), 3.83 (s, 3H), 3.85 (s, 6H), 6.63 (d, 2H), 6.73 (s, 2H), 7.86 (d, 2H).

Example 2

N-{4-[5,7-Dimethyl-4-(3,4,5-trimethoxyphenoxy)imidazo[5,1-f][1,2,4]triazin-2-yl]-phenyl}acetamide

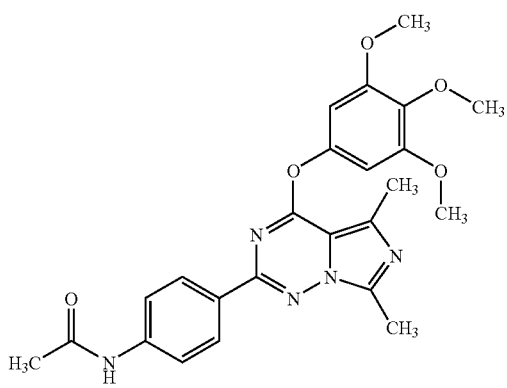

A solution of 10 mg (0.09 mmol) of acetic acid in dichloromethane is treated with 10 mg (0.09 mmol) of HOBt and 20 mg (0.21 mmol) of 4-methylmorpholine. The mixture is cooled to −20° C. and treated with 20 mg (0.09 mmol) of EDC. It is stirred for 30 min. Subsequently, 30 mg (0.07 mmol) of 4-[5,7-dimethyl-4-(3,4,5-tri-methoxyphenoxy)imidazo[5,1-f][1,2,4]triazin-2-yl]aniline from example 1 are added thereto at −20° C., and the mixture is stirred for 5 h at 20° C. The solution is then washed with aqueous 1 N potassium hydrogensulfate solution and saturated aqueous sodium hydrogencarbonate solution. The organic phase is dried and concentrated under reduced pressure. The residue is purified by flash chromatography (eluent:dichloromethane/methanol 100:1-80:1-60:1).

Yield: 15 mg (45% of theory)

MS (ESI): m/z=464 (M+H)$^+$

HPLC (method 1): $R_t$=3.84 min.

$^1$H-NMR (400 MHz, MeOH-d$_4$): δ=2.13 (s, 3H), 2.69 (s, 3H), 2.72 (s, 3H), 3.84 (s, 3H), 3.85 (s, 6H), 6.75 (s, 2H), 7.59 (d, 2H), 8.07 (d, 2H).

Example 3

N-[2-(4-Aminophenyl)-5,7-dimethylimidazo[5,1-f][1,2,4]triazin-4-yl]-N-(3,4,5-trimethoxyphenyl)amine

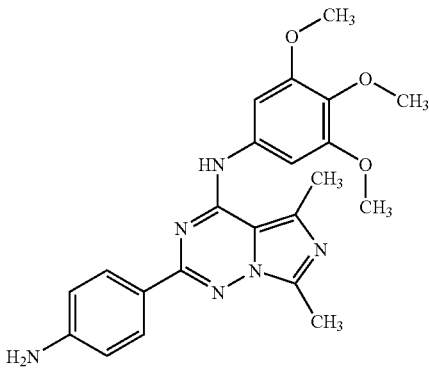

620 mg (1.38 mmol) of 5,7-dimethyl-2-(4-nitrophenyl)-N-(3,4,5-trimethoxyphenyl)-imidazo[5,1-f][1,2,4]triazin-4-amine from example 17A are hydrogenated in the presence of 200 mg of palladium on carbon (10% strength) analogously to example 1.

Yield: 290 mg (50% of theory)

MS (ESI): m/z=421 (M+H)$^+$

HPLC (method 1): $R_t$=3.50 min.

$^1$H-NMR (300 MHz, CDCl$_3$): δ=2.69 (s, 3H), 2.76 (s, 3H), 3.88 (s, 3H), 3.94 (s, 6H), 6.71 (d, 2H), 6.99 (s, 1H), 7.14 (s, 2H), 8.17 (d, 2H).

Example 4

N-(4-{5,7-Dimethyl-4-[(3,4,5-trimethoxyphenyl)amino]imidazo[5,1-f][1,2,4]triazin-2-yl}phenyl)acetamide

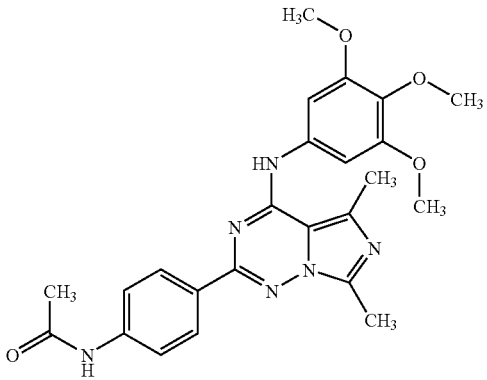

14.28 mg (0.24 mmol) of acetic acid, 32.14 mg (0.24 mmol) of HOBt, 72.17 mg (0.71 mmol) of 4-methylmorpholine, 45.6 mg (0.24 mmol) of EDC and 100 mg (0.24 mmol) of N-[2-(4-aminophenyl)-5,7-dimethylimidazo[5,1-f][1,2,4]triazin-4-yl]-N-(3,4,5-trimethoxyphenyl)amine from example 3 are reacted analogously to example 2. The work-up is carried out by HPLC separation.

Yield: 32 mg (29% of theory)

MS (ESI): m/z=463 (M+H)$^+$ $^1$H-NMR (300 MHz, CDCl$_3$): δ=2.21 (s, 3H), 2.71 (s, 3H), 2.78 (s, 3H), 3.89 (s, 3H), 3.94 (s, 6H), 7.04 (s, 1H), 7.12 (s, 2H), 7.59 (d, 2H), 8.32 (d, 2H).

Example 5

4-[5,7-Dimethyl-4-(3,4,5-trimethoxyphenoxy)imidazo[5,1-f][1,2,4]triazin-2-yl]-N,N-diethylaniline

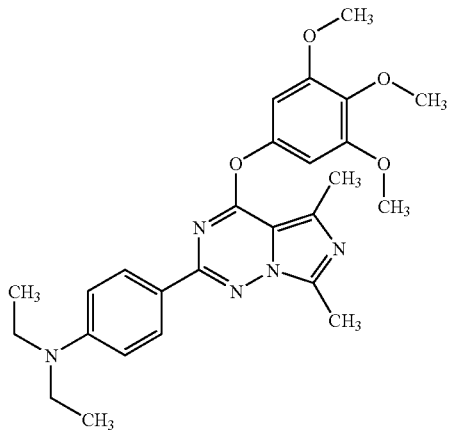

10 mg (0.08 mmol) of sodium cyanoborohydride and 10 mg (0.17 mmol) of acetaldehyde are added to a solution of 40 mg (0.08 mmol) of 4-[5,7-dimethyl-4-(3,4,5-trimethoxyphenoxy)imidazo[5,1-f][1,2,4]triazin-2-yl]aniline from example 1 in methanol and the mixture is stirred at 20° C. After expiration of the reaction time, the mixture is treated with 2N hydrochloric acid. The methanol is removed under reduced pressure and the aqueous residue is washed with dichloromethane, rendered alkaline using sodium hydroxide, and extracted twice with dichloromethane. The organic phase is dried over sodium sulfate and purified by chromatography (eluent:dichloromethane/methanol 80:1-60:1-40:1 plus a drop of NH$_4$OH)

Yield: 4 mg (10% of theory)
MS (ESI): m/z=478 (M+H)$^+$
HPLC (method 1): R$_t$=3.69 min.
$^1$H-NMR (300 MHz, MeOH-d$_4$): δ=1.11 (t, 6H), 2.66 (s, 3H), 2.68 (s, 3H), 3.36 (q, 4H), 3.83 (s, 3H), 3.85 (s, 6H), 6.61 (d, 2H), 6.69 (s, 2H), 7.88 (d, 2H).

Example 6

3-[5,7-Dimethyl-4-(3,4,5-trimethoxyphenoxy)imidazo[5,1-f][1,2,4]triazin-2-yl]-aniline

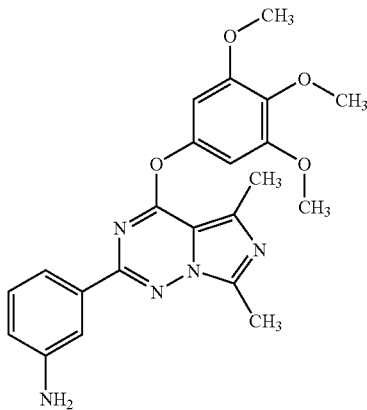

400 mg (0.89 mmol) of 5,7-dimethyl-2-(3-nitrophenyl)-4-(3,4,5-trimethoxyphenoxy)-imidazo[5,1-f][1,2,4]triazine from example 15A are hydrogenated in the presence of 120 mg of palladium on carbon (10% strength) analogously to example 1.

Yield: 350 mg (94% of theory)
MS (ESI): m/z=422 (M+H)$^+$
HPLC (method 1): R$_t$=3.69 min.
$^1$H-NMR (200 MHz, DMSO-d$_6$): δ=2.61 (s, 3H), 2.65 (s, 3H), 3.71 (s, 3H), 3.79 (s, 6H), 5.26 (br. s, 2H), 6.63–6.72 (d, 1H), 6.84 (s, 2H), 7.08 (t, 1H), 7.15–7.22 (d, 1H), 7.35 (s, 1H).

Example 7

N-[2-(3-Aminophenyl)-5,7-dimethylimidazo[5,1-f][1,2,4]triazin-4-yl]-N-(3,4,5-tri-methoxyphenyl)amine

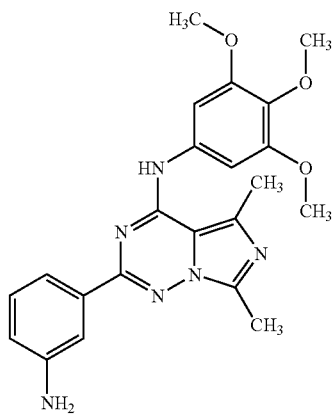

340 mg (0.76 mmol) of 5,7-dimethyl-2-(3-nitrophenyl)-N-(3,4,5-trimethoxyphenyl)-imidazo[5,1-f][1,2,4]triazin-4-amine from example 18A are hydrogenated in the presence of 110 mg of palladium on carbon (10% strength) analogously to example 1.

Yield: 231 mg (72% of theory)
MS (ESI): m/z=421 (M+H)$^+$
HPLC (method 1): R$_t$=3.51 min.
$^1$H-NMR (500 MHz, DMSO-d$_6$): δ=2.54 (s, 3H), 2.69 (s, 3H), 3.68 (s, 3H), 3.82 (s, 6H), 5.21 (s, 2H), 6.68 (d, 1H), 7.11 (t, 1H), 7.34 (s, 2H), 7.42 (d, 1H), 7.48 (s, 1H), 8.66 (s, 1H).

Example 8

5,7-Dimethyl-2-[4-(4-morpholinyl)phenyl]-4-(3,4,5-trimethoxyphenoxy)imidazo-[5,1-f][1,2,4]triazine

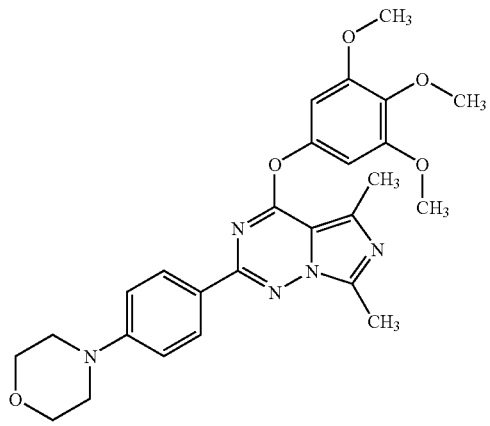

2 mg (0.004 mmol) of bis(dibenzylideneacetone)palladium(0) and 3 mg (0.004 mmol) of 2,2'-bis(diphenylphosphino)-1,1'-binaphthyl are introduced into a Schlenk vessel under argon. The mixture is dissolved in a little anhydrous toluene and stirred for 15 minutes at 20° C. (solution A).

28 mg (0.29 mmol) of sodium tert-butoxide are introduced into a second Schlenk tube under argon. Subsequently, 100 mg (0.21 mmol) of 2-(4-bromophenyl)-5,7-dimethyl-4-(3,4,5-trimethoxyphenoxy)imidazo[5,1-f][1,2,4]triazine from Exam-ple 16A, 22 mg (0.25 mmol) of morpholine and 2 ml of anhydrous toluene are added. Solution A is likewise added, and the whole is stirred overnight at 100° C. After cooling, the mixture is then filtered off with suction through a glass frit. The filtrate is concentrated to dryness under reduced pressure and purified by flash chromatography (cyclohexane/ethyl acetate 10:1-4:1-3:2-1:1).

Yield: 65 mg (64% of theory)

MS (ESI): m/z=492 (M+H)$^+$

HPLC (method 1): R$_t$=4.22 min.

$^1$H-NMR (300 MHz, DMSO-d$_6$): δ=2.60 (s, 3H), 2.64 (s, 3H), 3.17–3.24 (m, 4H), 3.68–3.75 (m, 7H, s at 3.72), 3.79 (s, 6H), 6.83 (s, 2H), 7.00 (d, 2H), 7.92 (d, 2H).

Example 9

N-{3-[5,7-Dimethyl-4-(3,4,5-trimethoxyphenoxy)imidazo[5,1-f][1,2,4]triazin-2-yl]-phenyl}acetamide

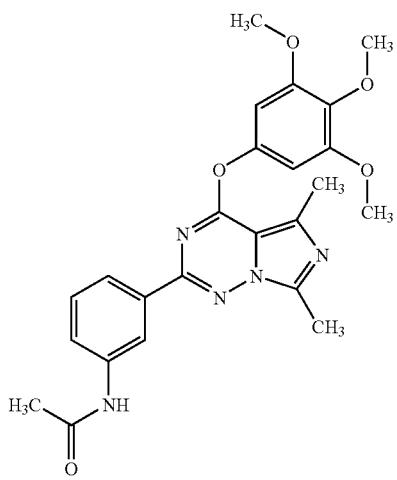

14.25 mg (0.24 mmol) of acetic acid, 32.06 mg (0.24 mmol) of HOBt, 72.00 mg (0.71 mmol) of 4-methylmorpholine, 50.03 mg (0.26 mmol) of EDC and 100 mg (0.24 mmol) of 3-[5,7-dimethyl-4-(3,4,5-trimethoxyphenoxy)imidazo[5,1-f][1,2,4]-triazin-2-yl]aniline from example 6 are reacted analogously to example 2.

Yield: 100 mg (91% of theory)

MS (ESI): m/z=464 (M+H)$^+$

HPLC (method 1): R$_t$=3.89 min.

$^1$H-NMR (300 MHz, CDCl$_3$): δ=2.19 (s, 3H), 2.79 (s, 3H), 2.84 (s, 3H), 3.88 (s, 6H), 3.92 (s, 3H), 6.59 (s, 2H), 7.37 (t, 1H), 7.80 (d, 1H), 7.89 (d, 1H), 8.09 (s, 1H).

Example 10

N-(3-{5,7-Dimethyl-4-[(3,4,5-trimethoxyphenyl)amino]imidazo[5,1-f][1,2,4]triazin-2-yl}phenyl)acetamide

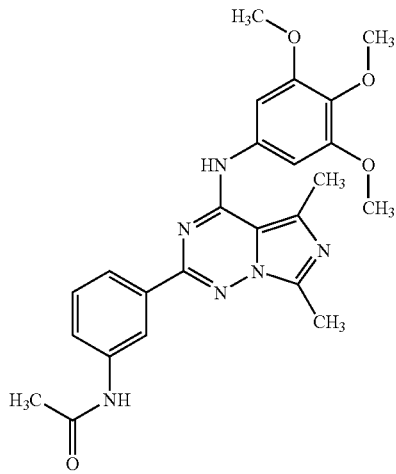

14 mg (0.21 mmol) of acetic acid, 31 mg (0.23 mmol) of HOBt, 63 mg (0.62 mmol) of 4-methylmorpholine, 44 mg (0.23 mmol) of EDC and 87 mg (0.21 mmol) of 3-[5,7-dimethyl-4-(3,4,5-trimethoxyphenoxy)imidazo[5,1-f][1,2,4]triazin-2-yl]-aniline from example 7 are reacted analogously to example 2.

Yield: 91 mg (95% of theory)

MS (ESI): m/z=463 (M+H)$^+$

HPLC (method 1): R$_t$=3.92 min.

$^1$H-NMR (300 MHz, DMSO-d$_6$): δ=2.06 (s, 3H), 2.59 (s, 3H), 2.70 (s, 3H), 3.69 (s, 3H); 3.82 (s, 6H), 7.31 (s, 2H), 7.40 (t, 1H), 7.75 (d, 1H), 7.91 (d, 1H), 8.38 (s, 1H), 8.81 (s, 1H), 10.06 (s, 1H).

Example 11

N-(3-{5,7-Dimethyl-4-[(3,4,5-trimethoxyphenyl)amino]imidazo[5,1-f][1,2,4]triazin-2-yl}phenyl)methanesulfonamide

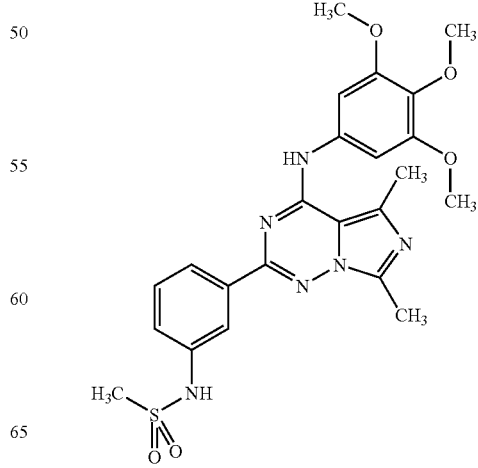

A solution of 80 mg (0.19 mmol) of 3-[5,7-dimethyl-4-(3,4,5-trimethoxyphenoxy)-imidazo[5,1-f][1,2,4]triazin-2-yl]aniline from example 7, 20 mg (0.19 mmol) of methanesulfonyl chloride and 40 mg (0.38 mmol) of triethylamine in dichloromethane is stirred overnight at 20° C. The mixture is washed with aqueous sodium hydrogencarbonate solution, and the organic phase is dried and purified by HPLC.

Yield: 19 mg (20% of theory)

MS (ESI): m/z=499 (M+H)+

HPLC (method 1): $R_t$=3.87 min.

$^1$H-NMR (300 MHz, DMSO-$d_6$): δ=2.59 (s, 3H), 2.70 (s, 3H), 2.98 (s, 3H), 3.69 (s, 3H); 3.82 (s, 6H), 7.26 (s, 2H), 7.36 (d, 1H), 7.48 (t, 1H), 7.98 (d, 1H), 8.11 (s, 1H), 8.76 (s, 1H), 9.83 (br. s, 1H).

Example 12

4-{5,7-Dimethyl-4-[(3,4,5-trimethoxyphenyl)amino]imidazo[5,1-f][1,2,4]triazin-2-yl}phenylformamide

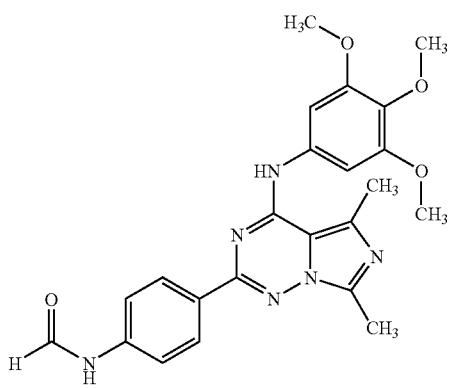

16 mg (0.24 mmol) of imidazole, 48 mg (0.48 mmol) of triethylamine and 11 mg (0.24 mmol) of formic acid are introduced into 4 ml dichloromethane under argon, cooled to 0° C. and treated dropwise with a solution of 30 mg (0.24 mmol) of oxalyl dichloride in dichloromethane. The mixture is allowed to warm to 20° C. and subsequently 100 mg (0.24 mmol) of N-[2-(4-aminophenyl)-5,7-dimethyl-imidazo[5,1-f][1,2,4]triazin-4-yl]-N-(3,4,5-trimethoxyphenyl)amine from example 3 are added thereto. It is stirred overnight and then washed with aqueous sodium hydrogencarbonate solution. The organic phase is dried and purified by flash chromatography (dichloromethane/methanol 100:1).

(Cf. T. Kitagawa et al., *Chem. Pharm. Bull.,* 42 (9), 1994, 1931–1934)

Yield: 56 mg (53% of theory)

MS (ESI): m/z=449 (M+H)+

HPLC (method 1): $R_t$=3.76 min.

$^1$H-NMR (300 MHz, DMSO-$d_6$): δ=2.69 (s, 3H), 2.76 (s, 3H), 3.70 (s, 3H); 3.82 (s, 6H), 7.29 (s, 2H), 7.69 (d, 2H), 8.20 (d, 2H), 8.32 (s, 1H), 8.71 (s, 1H), 10.36 (br. s, 1H).

Example 13

N-(4-{5,7-Dimethyl-4-[(3,4,5-trimethoxyphenyl)amino]imidazo[5,1-f][1,2,4]triazin-2-yl}phenyl)propanamide

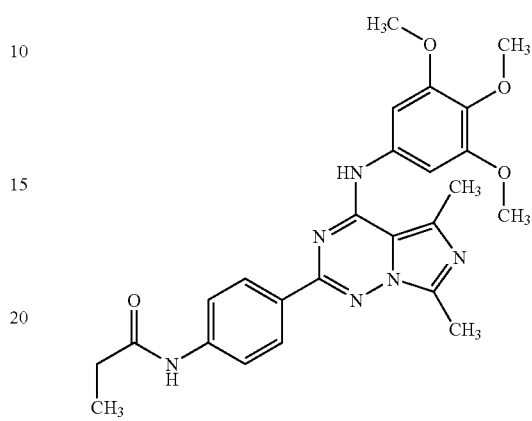

13 mg (0.17 mmol) of propionic acid, 23 mg (0.17 mmol) of HOBt, 47 mg (0.46 mmol) of 4-methylmorpholine, 33 mg (0.17 mmol) of EDC and 65 mg (0.21 mmol) of N-[2-(4-aminophenyl)-5,7-dimethylimidazo[5,1-f][1,2,4]triazin-4-yl]-N-(3,4,5-trimethoxyphenyl)amine from example 3 are reacted analogously to example 2.

Yield: 45 mg (61% of theory)

MS (ESI): m/z=477 (M+H)+

HPLC (method 1): $R_t$=4.10 min.

$^1$H-NMR (300 MHz, DMSO-$d_6$): δ=1.09 (t, 3H), 2.34 (q, 2H), 2.58 (s, 3H), 2.69 (s, 3H), 3.70 (s, 3H), 3.84 (s, 6H), 7.31 (s, 2H), 7.70 (d, 2H), 8.18 (d, 2H), 8.69 (br. s, 1H), 10.0 (br. s, 1H).

Example 14

$N^1$-(4-{5,7-Dimethyl-4-[(3,4,5-trimethoxyphenyl)amino]imidazo[5,1-f][1,2,4]-triazin-2-yl}phenyl)glycinamide

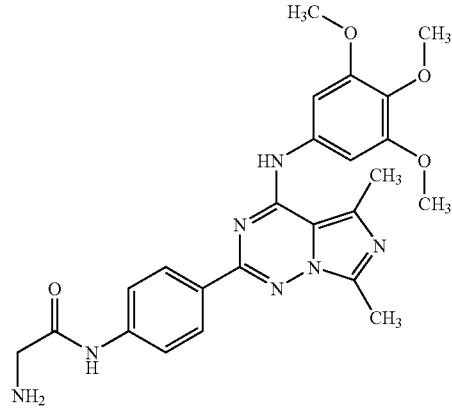

740 mg (6.49 mmol) of trifluoroacetic acid are added dropwise to a solution of 40 mg (0.07 mmol) of example 20A in 5 ml of dichloromethane and the mixture is stirred for 6 h at 20° C. After stripping off the solvent, the residue is dried in a high vacuum and purified by HPLC.

Yield: 27 mg (81% of theory)

MS (ESI): m/z=478 (M+H)$^+$

HPLC (method 1): R$_t$=3.58 min.

$^1$H-NMR (400 MHz, MeOH-d$_4$): δ=2.74 (s, 3H), 2.80 (s, 3H), 3.84 (s, 3H), 3.91 (s, 2H), 3.92 (s, 6H), 7.30 (s, 2H), 7.71 (d, 2H), 8.31 (d, 2H).

Example 15

N-(4-{5,7-Dimethyl-4-[(3,4,5-trimethoxyphenyl)amino]imidazo[5,1-f][1,2,4]triazin-2-yl}phenyl)-2-hydroxyacetamide

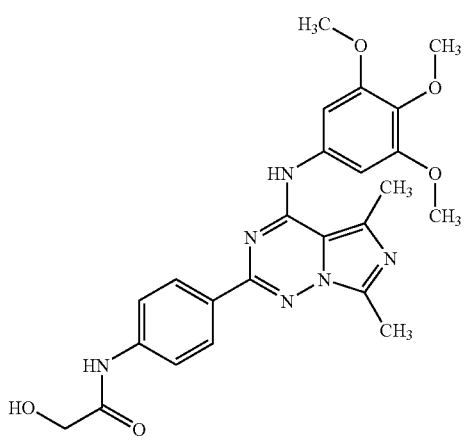

A solution of are 50 mg (0.12 mmol) of N-[2-(4-aminophenyl)-5,7-dimethyl-imidazo[5,1-f][1,2,4]triazin-4-yl]-N-(3,4,5-trimethoxyphenyl)amine from example 3 in DMF is treated with 18 mg (0.24 mmol) of glycolic acid, 90 mg (0.24 mmol) of HATU and 46 mg (0.24 mmol) of EDC. It is stirred overnight at 20° C. The solvent is removed under reduced pressure and the residue is purified by HPLC.

Yield: 25 mg (44% of theory)

MS (ESI): m/z=479 (M+H)$^+$

HPLC (method 1): R$_t$=3.76 min.

$^1$H-NMR (300 MHz, MeOH-d$_4$): δ=2.76 (s, 3H), 2.82 (s, 3H), 3.87 (s, 3H), 3.95 (s, 6H), 4.20 (s, 2H), 7.32 (s, 2H), 7.74 (d, 2H), 8.29 (d, 2H).

Example 16

4-({4-[5,7-Dimethyl-4-(3,4,5-trimethoxyphenoxy)imidazo[5,1-f][1,2,4]triazin-2-yl]-phenyl}amino)-4-oxobutanoic acid

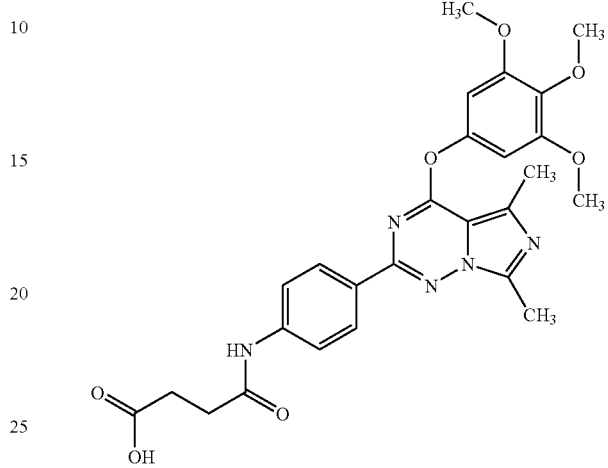

A solution of 100 mg (0.24 mmol) of N-[2-(4-aminophenyl)-5,7-dimethyl-imidazo[5,1-f][1,2,4]triazin-4-yl]-N-(3,4,5-trimethoxyphenyl)amine from example 3 and 77 mg (0.76 mmol) of dihydro-2,5-furandione dissolved in dichloromethane is stirred under reflux for 16 h. The mixture is concentrated to dryness and the residue is purified by flash chromatography using the eluent dichloromethane/methanol.

Yield: 127 mg (quant.)

LC-MS (method 2): R$_t$=2.59 min.

MS (ESI$^+$): m/z=522 [M+H]$^+$

MS (ESI-): m/z=520 [M-H]$^{31}$ $^1$H-NMR (200 MHz, DMSO-d$_6$): δ=2.46–2.61 (m, 4H, under DMSO signal), 2.62 (s, 3H), 2.66 (s, 3H), 3.72 (s, 3H), 3.79 (s, 6H), 6.86 (s, 2H), 7.68 (d, 2H) 8.00 (d, 2H), 10.22 (s, 1H), 12.23 (br. s, 1H).

Example 17

5,7-Dimethyl-2-[4-(1-pyrrolidinyl)phenyl]-4-(3,4,5-trimethoxyphenoxy)imidazo-[5,1-f][1,2,4]triazine Example 18

5,7-Dimethyl-2-[4-(1-piperidinyl)phenyl]-4-(3,4,5-trimethoxyphenoxy)imidazo-[5,1-f][1,2,4]triazine General preparation procedure for the compounds of examples 17 and 18:

1 eq. of the compound from example 16A is suspended in xylene with 1.2 eq. of amine, 1.4 eq. of sodium tert-butoxide, 0.02 eq. of BINAP and 0.02 eq. of bis(dibenzylideneacetone)palladium. The mixture is stirred for 16 h at 140° C. The solvent is then removed in vacuo, the residue is taken up in toluene and the mixture is again concentrated to dryness in vacuo. The product is purified by HPLC.

| Example | Structure | Mixture | Yield | Analytics |
|---|---|---|---|---|
| 17 | 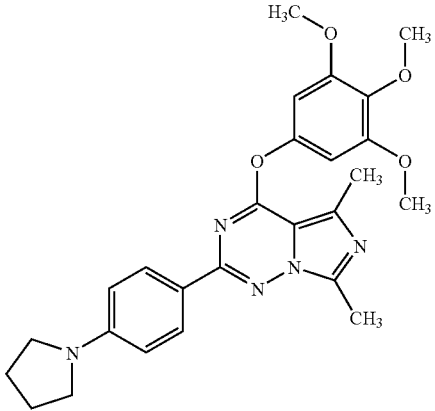 | 100 mg (0.21 mmol) of 16A, 17.3 mg (0.25 mmol) of pyrrol-idine and equi-molar amounts of the other reagents (see above). | 22 mg 23% of theory | MS (ESI): m/z = 476 [M + H]$^+$ HPLC (method 1): $R_t$ = 4.73 min. $^1$H-NMR (200 MHz, DMSO-$d_6$): 1.91–2.20 (m, 4H), 2.59 (s, 3H), 2.62 (s, 3H), 3.22–3.32 (m, 4H), 3.72 (s, 3H), 3.79 (s, 6H), 6.57 (d, 2H), 6.83 (s, 2H), 7.88 (d, 2H). |
| 18 | 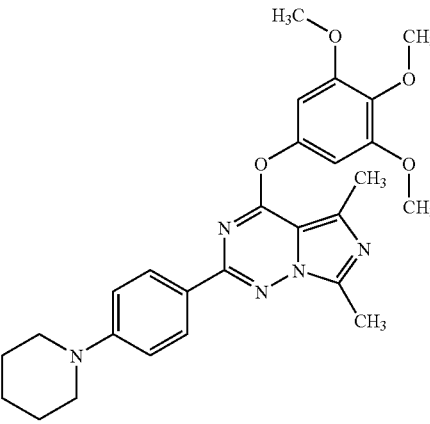 | 100 mg (0.21 mmol) of 16A, 21.1 mg (0.25 mmol) piperidine and equimolar amounts of the other reagents (see above). | 18 mg 18% of theory | MS (ESI): m/z = 490 [M + H]$^+$ HPLC (method 1): $R_t$ = 4.02 min. $^1$H-NMR (200 MHz, DMSO-$d_6$): 1.52–1.64 (m, 6H), 2.60 (s, 3H), 2.63 (s, 3H), 3.23–3.32 (m, 4H), 3.72 (s, 3H), 3.79 (s, 6H), 6.83 (s, 2H), 6.97 (d, 2H), 7.88 (d, 2H). |

Example 19

N-{4-[5,7-Dimethyl-4-(3,4,5-trimethoxyphenoxy)imidazo[5,1-f][1,2,4]triazin-2-yl]-phenyl}propanamide Example 20

N-{4-[5,7-Dimethyl-4-(3,4,5-trimethoxyphenoxy)imidazo[5,1-f][1,2,4]triazin-2-yl]-phenyl}cyclopropanecarboxamide Example 21

N-{4-[5,7-Dimethyl-4-(3,4,5-trimethoxyphenoxy)imidazo[5,1-f][1,2,4]triazin-2-yl]-phenyl}cyclopentanecarboxamide Example 22

N-{4-[5,7-Dimethyl-4-(3,4,5-trimethoxyphenoxy)imidazo[5,1-f][1,2,4]triazin-2-yl]-phenyl}-2-hydroxypropanamide Example 23

N-{4-[5,7-Dimethyl-4-(3,4,5-trimethoxyphenoxy)imidazo[5,1-f][1,2,4]triazin-2-yl]-phenyl}tetrahydro-2-furancarboxamide Example 24

N-{4-[5,7-Dimethyl-4-(3,4,5-trimethoxyphenoxy)imidazo[5,1-f][1,2,4]triazin-2-yl]-phenyl}tetrahydro-3-furancarboxamide Example 25

N-{4-[5,7-Dimethyl-4-(3,4,5-trimethoxyphenoxy)imidazo[5,1-f][1,2,4]triazin-2-yl]-phenyl}tetrahydro-2H-pyran-4-carboxamide Example 26

N$^1$-(4-{5,7-Dimethyl-4-[(3,4,5-trimethoxyphenyl)amino]imidazo[5,1-f][1,2,4]triazin-2-yl}phenyl)-β-alaninamide

Example 27

N¹-{4-[5,7-Dimethyl-4-(3,4,5-trimethoxyphenoxy) imidazo[5,1-f][1,2,4]triazin-2-yl]-phenyl}-N²,N²-dimethylglycinamide

Example 28

N-{4-[5,7-Dimethyl-4-(3,4,5-trimethoxyphenoxy) imidazo[5,1-f][1,2,4]triazin-2-yl]-phenyl}-2-(4-methyl-1-piperazinyl)acetamide General synthesis procedure for the compounds of examples 19 to 28:

1 eq. of compounds from example 1 or 3 is dissolved in dichloromethane with 1.2 eq. of acid, 1.2 of HATU, 1.2 eq of EDC×HCl and stirred for 16 h at RT. The solvent is then removed in vacuo, the residue is taken up in toluene and the solution is again concentrated to dryness in vacuo. The product is purified by HPLC.

After purification, the compound from example 26 is dissolved in dichloromethane and treated with 10 eq. of trifluoroacetic acid. The mixture is then stirred for 6 h at RT, the solvent is subsequently removed under reduced pressure and the product is purified by HPLC.

| Example | Structure | Mixture | Yield | Analytics |
|---|---|---|---|---|
| 19 | 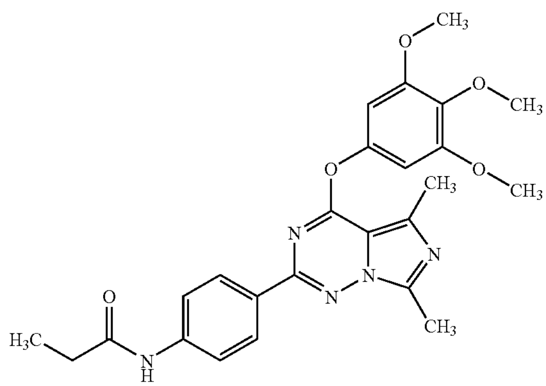 | 100 mg (0.24 mmol) of Ex.1, 21.1 mg (0.28 mmol) of propionic acid and equimolar amounts of the other reagents. | 53 mg 47% of theory | LC-MS (method 3): MS (ESI⁺): m/z = 478 [M + H]⁺, MS (ESI⁻): m/z = 476 [M − H]. HPLC (method 1): R$_t$ = 3.98 min. ¹H-NMR (300 MHz, CDCl$_3$): 1.26 (t, 3H), 2.42 (q, 2H), 2.73 (s, 3H), 2.76 (s, 3H), 3.87 (s, 6H), 3.91 (s, 3H), 6.62 (s, 2H), 7.22 (s, 1H), 7.56 (d, 2H), 8.12 (d, 2H). |
| 20 | 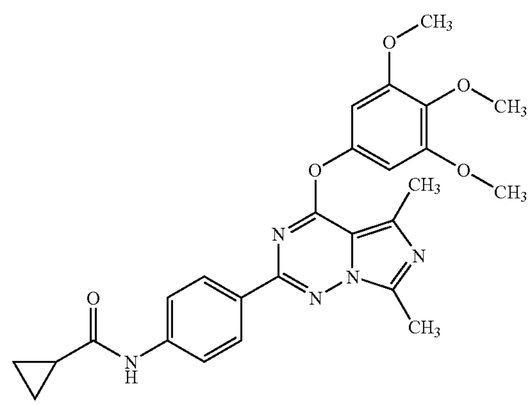 | 100 mg (0.24 mmol) of Ex.1, 24.5 mg (0.28 mmol) of cyclopropane-carboxylic acid and equimolar amounts of the other reagents. | 38 mg 33% of theory | LC-MS (method 3): MS (ESI⁺): m/z = 490 [M + H]⁺, MS (ESI⁻): m/z = 488 [M − H]⁻. HPLC (method 1): R$_t$ = 4.06 min. ¹H-NMR (300 MHz, CDCl$_3$): 0.84–0.91 (m, 2H), 1.08–1.15 (m, 2H), 1.52 (m, 1H), 2.73 (s, 3H), 2.77 (s, 3H), 3.87 (s, 6H), 3.91 (s, 3H), 6.62 (s, 2H), 7.47 (s, 1H), 7.57 (d, 2H), 8.12 (d, 2H). |
| 21 | 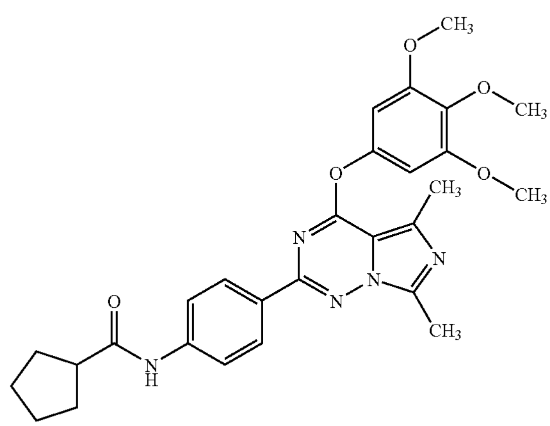 | 100 mg (0.24 mmol) of Ex.1, 32.5 mg (0.28 mmol) of cyclopentane-carboxylic acid and equimolar amounts of the other reagents. | 44 mg 36% of theory | LC-MS (method 3): MS(ESI⁺): m/z = 518 [M + H]⁺, MS (ESI⁻): m/z = 516 [M − H]⁻. HPLC (method 1): R$_t$ = 4.33 min. ¹H-NMR (300 MHz, CDCl$_3$): 1.51–2.01 (m, 9H), 2.74 (s, 3H), 2.77 (s, 3H), 3.87 (s, 6H), 3.91 (s, 3H), 6.62 (s, 2H), 7.25 (s, 1H), 7.58 (d, 2H), 8.12 (d, 2H). |

| Example | Structure | Mixture | Yield | Analytics |
|---|---|---|---|---|
| 22 | (structure) | 100 mg (0.24 mmol) of Ex.1, 25.7 mg (0.28 mmol) of (+/−)-2-hydroxyl-propanoic acid and equimolar amounts of the other reagents. | 44 mg 38% of theory | LC-MS (method 3): MS (ESI$^+$): m/z = 494 [M + H]$^+$, MS (ESI$^-$): m/z = 492 [M − H]$^-$. HPLC (method 1): R$_t$ = 3.77 min. $^1$H-NMR (300 MHz, CDCl$_3$): 1.56 (d, 3H), 2.75 (s, 3H), 2.78 (s, 3H), 3.88 (s, 6H), 3.92 (s, 3H), 4.42 (q, 1H), 6.62 (s, 2H), 7.63 (d, 2H), 8.13 (d, 2H), 8.56 (s, 1H). |
| 23 | (structure) | 100 mg (0.24 mmol) of Ex.1, 33.1 mg (0.28 mmol) of tetrahydro-2-furan-carboxylic acid and equimolar amounts of the other reagents. | 81 mg 66% of theory | LC-MS (method 3): MS (ESI$^+$): m/z = 520 [M + H]$^+$, MS (ESI$^-$): m/z = 518 [M − H]$^-$. HPLC (method 1): R$_t$ = 4.03 min. $^1$H-NMR (300 MHz, CDCl$_3$): 1.88–2.04 (m, 2H), 2.13–2.25 (m, 1H), 2.30–2.44 (m, 1H), 2.74 (s, 3H), 2.78 (s, 3H), 3.87 (s, 6H), 3.91 (s, 3H), 3.93–4.12 (m, 2H), 4.47 (m, 1H), 6.62 (s, 2H), 7.63 (d, 2H), 8.14 (d, 2H), 8.57 (s, 1H). |
| 24 | (structure) | 100 mg (0.24 mmol) of Ex.1, 33.1 mg (0.28 mmol) of tetrahydro-3-furan-carboxylic acid and equimolar amounts of the other reagents. | 57 mg 46% of theory | LC-MS (method 3): MS (ESI$^+$): m/z = 520 [M + H]$^+$, MS (ESI$^-$): m/z = 518 [M − H]$^-$. HPLC (method 1): R$_t$ = 4.89 min. $^1$H-NMR (300 MHz, CDCl$_3$): 2.28 (m, 2H), 2.74 (s, 3H), 2.78 (s, 3H), 3.06 (m, 1H), 3.82–4.12 (m, 13H, s at 3.87 and 3.91), 6.61 (s, 2H), 7.56 (m, 3H), 8.13 (d, 2H). |

-continued

| Example | Structure | Mixture | Yield | Analytics |
|---|---|---|---|---|
| 25 | 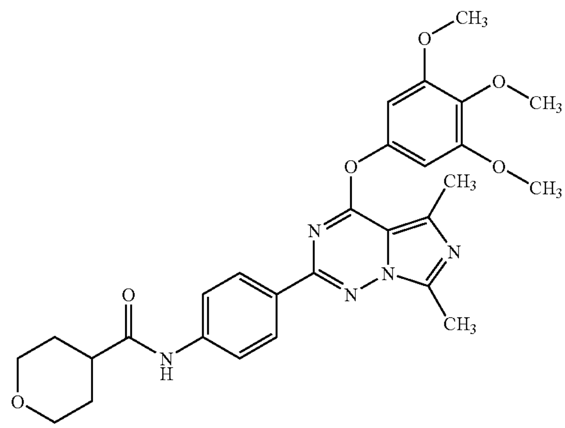 | 100 mg (0.24 mmol) Ex.1, 37.1 mg (0.28 mmol) of tetrahydropyran carboxylic acid and equimolar amounts of the other reagents. | 40 mg 32% of theory | LC-MS (method 3): MS (ESI$^+$): m/z = 534 [M + H]$^+$, MS (ESI$^-$): m/z = 532 [M − H].− HPLC (method 1): R$_t$ = 3.93 min. $^1$H-NMR (300 MHz, CDCl$_3$): 1.81–2.01 (m, 4H), 2.52 (m, 1H), 2.74 (s, 3H), 2.78 (s, 3H), 3.46 (m, 2H), 3.87 (s, 6H), 3.91 (s, 3H), 4.07 (m, 2H), 6.61 (s, 2H), 7.58 (d, 2H), 8.12 (d, 2H). |
| 26 | 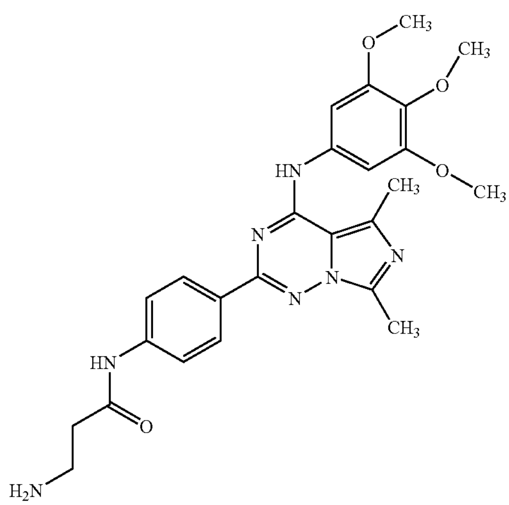 | 94 mg (0.22 mmol) of Ex.3, 84.6 mg (0.45 mmol) of N-(tert-butoxy-carbonyl)-β-alanine, 170 mg (0.45 mmol) of HATU, 85.7 mg (0.45 mmol) of EDC x HCl, 800 µl (10.4 mmol) of trifluoroacetic acid | 24 mg 22% of theory | MS (ESI): m/z = 492 (M + H)$^+$, HPLC (method 1): R$_t$ = 3.61 min., $^1$H-NMR (400 MHz, CD$_3$OD): 2.58–2.65 (m, 5H, s at 2.61), 2.70 (s, 3H), 3.01–3.10 (m, 2H), 3.80 (s, 3H), 3.88 (s, 6H), 7.28 (s, 2H), 7.62 (d, 2H), 8.21 (d, 2H). |
| 27 | 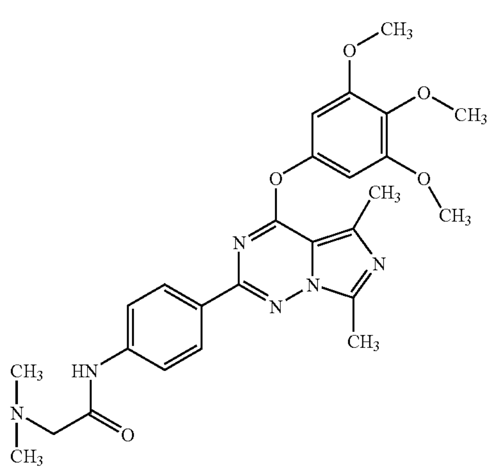 | 100 mg (0.24 mmol) of Ex.1, 29.4 mg (0.28 mmol) of N,N-dimethyl-glycine and equimolar amounts of the other reagents. | 12 mg 10% of theory | MS(ESI): m/z = 507 (M+H)$^+$, HPLC (method 1): R$_t$ = 3.63 min., $^1$H-NMR (200 MHz, DMSO-d$_6$): 2.62 (s, 3H), 2.67 (s, 3H), 2.86 (s, 6H), 3.72 (s, 3H), 3.79 (s, 6H), 4.12 (s, 2H), 6.86 (s, 2H), 7.70 (d, 2H), 8.06 (d, 2H), 10.74 (s, 1H). |

| Example | Structure | Mixture | Yield | Analytics |
|---|---|---|---|---|
| 28 | 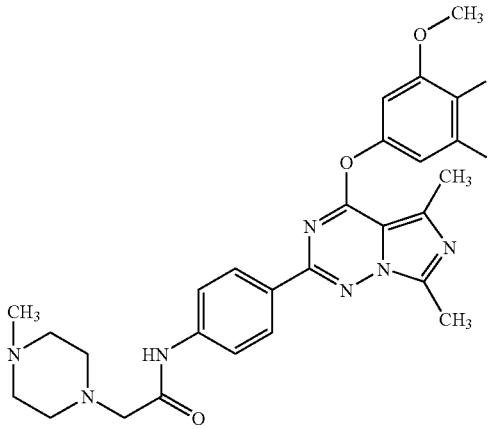 | 100 mg (0.21 mmol) of Ex. 1, 45.0 mg (0.28 mmol) of (4-methyl-1-piperazinyl)-ethanoic acid and equimolar amounts of the other reagents. | 61 mg 46% of theory | MS (ESI): m/z = 562 [M + H]$^+$ HPLC (method 1): R$_t$ = 3.59 min. $^1$H-NMR (200 MHz, CDCl$_3$): 2.45 (s, 3H), 2.67–2.81 (m, 14H, s at 2.73 and 2.76), 3.19 (d, 2H), 3.88 (s, 6H), 3.92 (s, 3H), 6.61 (s, 2H), 7.61 (d, 2H), 8.15 (d, 2H), 9.13 (s, 1H). |

The invention claimed is:

1. A compound of the formula

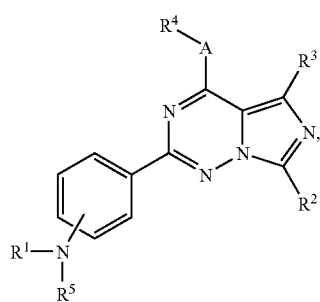

in which

R$^1$ denotes hydrogen or C$_1$–C$_6$-alkyl,

R$^5$ denotes hydrogen, formyl, C$_1$–C$_6$-alkyl, (C$_1$–C$_6$-alkyl)carbonyl, C$_1$–C$_6$-alkylsulfonyl, (C$_3$–C$_8$-cycloalkyl)carbonyl or (3- to 8-membered heterocyclyl)carbonyl, where alkylcarbonyl can be substituted by up to 3 substituents—independently of one another selected from the group consisting of halogen, hydroxyl, amino, carboxyl, C$_1$–C$_6$-alkoxy, C$_6$–C$_{10}$-aryl, C$_1$–C$_6$-alkylamino and a 3- to 8-membered heterocyclyl substituted by up to 3 C$_1$–C$_3$-alkyl substituents— or

R$^1$ and R$^5$, together with the nitrogen atom to which they are bonded, denote a 5- to 8-membered heterocycle, which can be substituted by up to 3 substituents—independently of one another selected from the group consisting of halogen, hydroxyl, C$_1$–C$_6$-alkyl, C$_1$–C$_6$-alkoxy, C$_6$–C$_{10}$-aryl, amino and C$_1$–C$_6$-alkylamino R$^2$ denotes C$_1$–C$_6$-alkyl or C$_3$–C$_4$-cycloalkyl, R$^3$ denotes methyl, A denotes an oxygen atom or NH, and R$^4$ denotes C$_6$–C$_{10}$-aryl, which can be substituted by up to 3 substituents—independently of one another selected from the group consisting of halogen, formyl, carboxyl, carbamoyl, cyano, hydroxyl, trifluoromethyl, trifluoromethoxy, nitro, C$_1$–C$_6$-alkyl, C$_1$–C$_6$-alkoxy, 1,3-dioxapropan-1,3-diyl, C$_1$–C$_6$-alkylthio and —NR$^6$R$^7$—, in which R$^6$ and R$^7$ independently of one another represent hydrogen, C$_1$–C$_6$-alkyl or (C$_1$–C$_6$-alkyl)carbonyl, or salt thereof.

2. The compound of claim 1, wherein

R$^1$ denotes hydrogen,

R$^5$ denotes hydrogen, (C$_3$–C$_6$-cycloalkyl)carbonyl, (4- to 6-membered heterocyclyl)carbonyl or (C$_1$–C$_3$-alkyl)carbonyl, where alkylcarbonyl can be monosubstituted by hydroxyl or amino, R$^2$ denotes C$_1$–C$_6$-alkyl, R$^3$ denotes methyl, A denotes an oxygen atom or NH, and R$^4$ denotes phenyl, which can be substituted by up to 3 substituents, independently of one another selected from the group consisting of halogen, C$_1$–C$_6$-alkyl and C$_1$–C$_6$-alkoxy, or salt thereof.

3. The compound of claim 1, wherein

R$^1$ denotes hydrogen,

R$^5$ denotes hydrogen, (C$_3$–C$_6$-cycloalkyl)carbonyl, (4- to 6-membered heterocyclyl)carbonyl or (C$_1$–C$_3$-alkyl)carbonyl, where alkylcarbonyl can be monosubstituted by hydroxyl or amino, R$^2$ denotes C$_1$–C$_6$-alkyl, R$^3$ denotes methyl, A denotes an oxygen atom or NH, and R$^4$ denotes phenyl, which can be substituted by 1 to 3 (C$_1$–C$_6$)-alkoxy radicals, and or salt thereof.

4. A process for the preparation of a compound of claim 1, wherein

[A] a compound of the formula

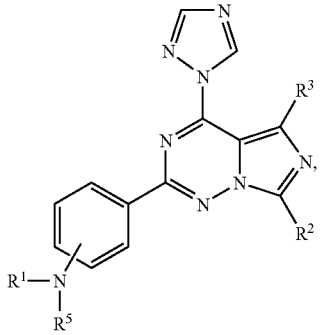
(II)

in which
R¹, R⁵, R² and R³ have the meanings indicated in claim 1, is reacted with a compound of the formula

(III)

in which
R⁴ and A have the meanings indicated in claim 1, or

[B] a compound of the formula

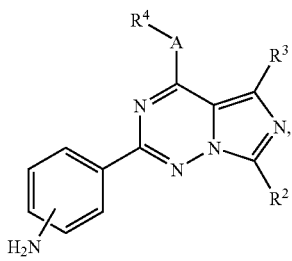
(Ia)

in which
R², R³, R⁴ and A have the meanings indicated in claim 1, is reacted with a compound of the formula

(IV)

in which
R⁵ has the meaning indicated above and
X¹ represents halogen, or hydroxyl,
to give a compound of the formula

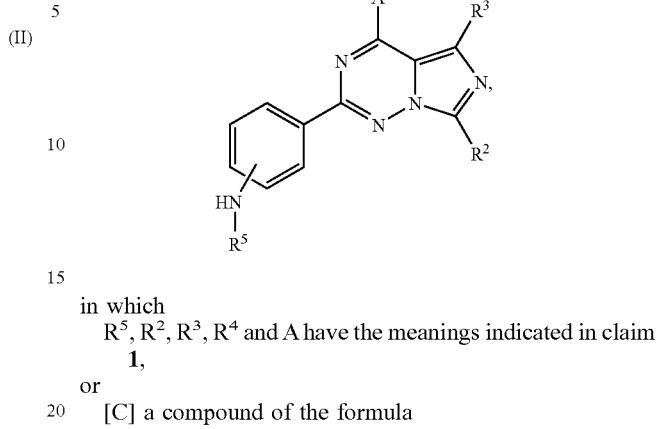
(Ib)

in which
R⁵, R², R³, R⁴ and A have the meanings indicated in claim 1, or

[C] a compound of the formula

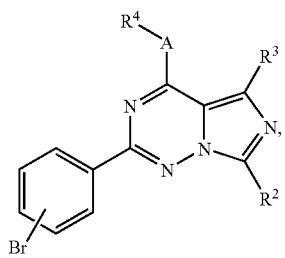
(V)

in which
R², R³, R⁴ and A have the meanings indicated in claim 1, is reacted with a compound of the formula

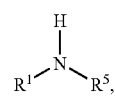
(VI)

in which
R¹ and R⁵ have the meanings indicated in claim 1, and optionally the compound (I) resulting from [A], [B] or [C] is reacted with the appropriate (i) solvents and/or (ii) bases or acids to give the salt thereof.

5. A medicament containing one or more of the compounds as claimed in any one of claims 1 to 3 and one or more pharmaceutically tolerable, essentially nontoxic vehicle or excipient.

6. A method for the treatment of Parkinson's disease comprising administering to a human or animal an effective amount of a compound of any one of claims 1 to 3.

7. A method for the treatment of schizophrenia comprising administering to a human or animal an effective amount of a compound of any one of claims 1 to 3.

8. The process of claim 4, wherein X¹ is bromine or chlorine.

* * * * *